US012708663B2

(12) United States Patent
Aspelund et al.

(10) Patent No.: US 12,708,663 B2
(45) Date of Patent: Aug. 18, 2026

(54) INFLUENZA VIRUS ENCODING A TRUNCATED NS1 PROTEIN AND A SARS-COV RECEPTOR BINDING DOMAIN

(71) Applicant: Vivaldi Biosciences Inc., Fort Collins, CO (US)

(72) Inventors: Amy Aspelund, Fort Collins, CO (US); Thomas Muster, Vienna (AT); Markus Wolschek, Vienna (AT)

(73) Assignee: VIVALDI BIOSCIENCES INC., Fort Collins, CO (US)

( * ) Notice: Subject to any disclaimer, the term of this patent is extended or adjusted under 35 U.S.C. 154(b) by 593 days.

(21) Appl. No.: 18/036,631

(22) PCT Filed: Nov. 17, 2021

(86) PCT No.: PCT/US2021/059788

§ 371 (c)(1),
(2) Date: May 11, 2023

(87) PCT Pub. No.: WO2022/109068

PCT Pub. Date: May 27, 2022

(65) Prior Publication Data

US 2023/0414745 A1 Dec. 28, 2023

Related U.S. Application Data

(60) Provisional application No. 63/114,941, filed on Nov. 17, 2020.

(51) Int. Cl.

| | |
|---|---|
| ***A61K 39/145*** | (2006.01) |
| ***A61K 39/00*** | (2006.01) |
| ***A61K 39/12*** | (2006.01) |
| ***A61K 45/06*** | (2006.01) |
| ***A61P 31/14*** | (2006.01) |
| ***C07K 16/104*** | (2026.01) |
| ***C12N 7/00*** | (2006.01) |

(52) U.S. Cl.

CPC ............ *A61K 39/12* (2013.01); *A61K 39/145* (2013.01); *A61P 31/14* (2018.01); *C07K 16/104* (2026.01); *C12N 7/00* (2013.01); *A61K 2039/5254* (2013.01); *A61K 2039/545* (2013.01)

(58) Field of Classification Search

CPC ............ A61K 2039/5254; A61K 39/12; A61K 39/145; A61K 2039/57; A61K 39/39

See application file for complete search history.

(56) References Cited

U.S. PATENT DOCUMENTS

2020/0237899 A1 7/2020 Kawaoka et al.

FOREIGN PATENT DOCUMENTS

| | | | |
|---|---|---|---|
| CN | 111560074 | A | 8/2020 |
| CN | 111569057 | A | 8/2020 |
| CN | 111732638 | A | 10/2020 |
| WO | 2013177444 | A2 | 11/2013 |
| WO | 2020152318 | A2 | 7/2020 |
| WO | 2021160036 | A1 | 8/2021 |

OTHER PUBLICATIONS

Ali, A et al., "Influenza Virus Assembly: Effect of Influenza Virus Glycoproteins on the Membrane Association of M1 Protein", J. Virol., 2000, vol. 74, No. 18, pp. 8709-8719.

Anonymous, "The University of Hong Kong (HKU)", Genetic Engineering & Biotechnology News, May 18, 2020, XP055888754.

Anonymous, "A Phase I Clinical Trial of Influenza virus Vector COVID-19 Vaccine for intranasal Spray (DelNS1-2019-nCOV-RBD-OPT1)", Chinese Clinical Trial Register (ChiCTR), Registration No. ChiCTR2000037782, Sep. 2020, XP055889557.

Anonymous, "A Phase II Clinical Trial of Influenza virus Vector COVID-19 Vaccine for intranasal Spray (DeINS1-2019-nCOV-RBD-OPT1)", Chinese Clinical Trial Register (ChiCTR), Registration No. ChiCTR2000039715, Nov. 2020, XP055889884.

Barman, S et al. "Transport of viral proteins to the apical membranes and interaction of matrix protein with glycoproteins in the assembly of influenza viruses", 2001, Virus Res., vol. 77, No. 1, pp. 61-69.

Barman, S et al., "Role of Transmembrane Domain and Cytoplasmic Tail Amino Acid Sequences of Influenza A Virus Neuraminidase in Raft Association and Virus Budding", 2004, J. Virol., vol. 78, No. 10, pp. 5258-5269.

Blok, J et al "Variation in the Membrane-Insertion and "Stalk" Sequences in Eight Subtypes of Influenza Type A Virus Neuraminidase", Biochemistry, 1982, vol. 21, pp. 4001-4007.

Dreyfus, C et al. "Highly Conserved Protective Epitopes on Influenza B Viruses", 2012, Science, vol. 337, No. 6100, pp. 1343-1348.

Ekiert, D C et al. "A Highly Conserved Neutralizing Epitope on Group 2 Influenza A Viruses", 2011, Science, vol. 333, No. 6044, pp. 843-850.

Enami, M et al. "Influenza Virus Hemagglutinin and Neuraminidase Glycoproteins Stimulate the Membrane Association of the Matrix Protein", 1996, J. Virol., vol. 70, No. 10, pp. 6653-6657.

Ferko, B et al. "Immunogenicity and Protection Efficacy of Replication-Deficient Influenza A Viruses with Altered NS1 Genes", 2004, J. Virol., vol. 78, No. 23, pp. 13037-13045.

García-Sastre A. et al. "The cytoplasmic tail of the neuraminidase protein of influenza A virus does not play an important role in the packaging of this protein into viral envelopes", 1995, Virus Res., vol. 37, pp. 37-47.

(Continued)

*Primary Examiner* — Barry A Chestnut

(74) *Attorney, Agent, or Firm* — LOZA & LOZA, LLP; Michael Fedrick

(57) ABSTRACT

The present invention refers to a recombinant influenza vims encoding a fusion protein comprising a truncated NS1 protein and a SARS-CoV receptor binding domain, specifically a SARS-CoV-2 RBD, and its use for prophylactic treatment, a pharmaceutical preparation comprising said virus for use in prime boost vaccination and a two-component vaccine for prime boost vaccination.

20 Claims, 12 Drawing Sheets

Figure 1:
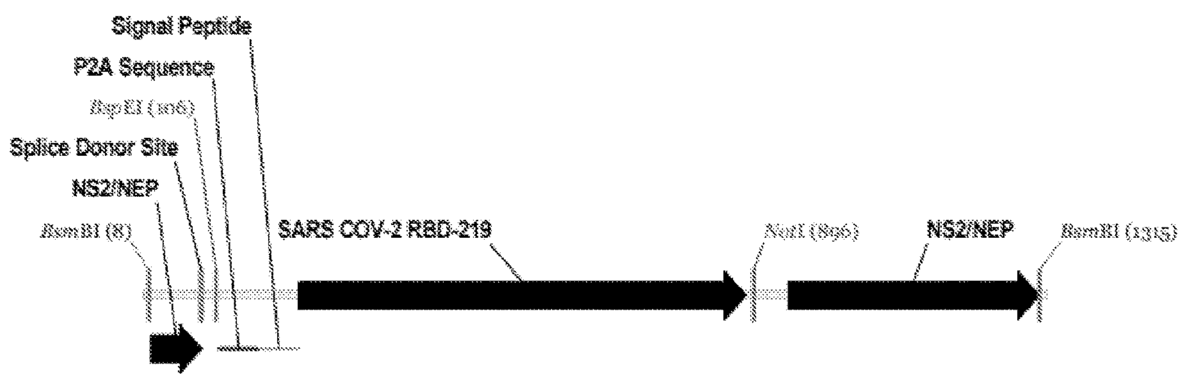
Figure 1:
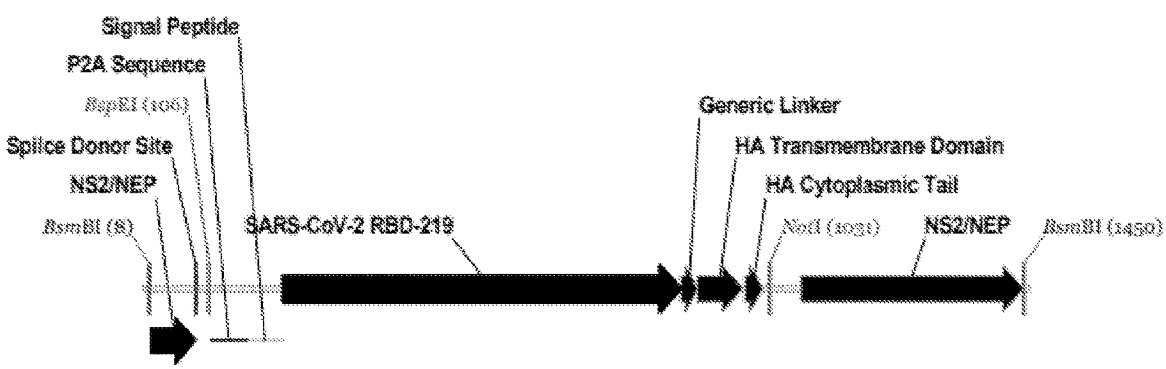
Figure 1:
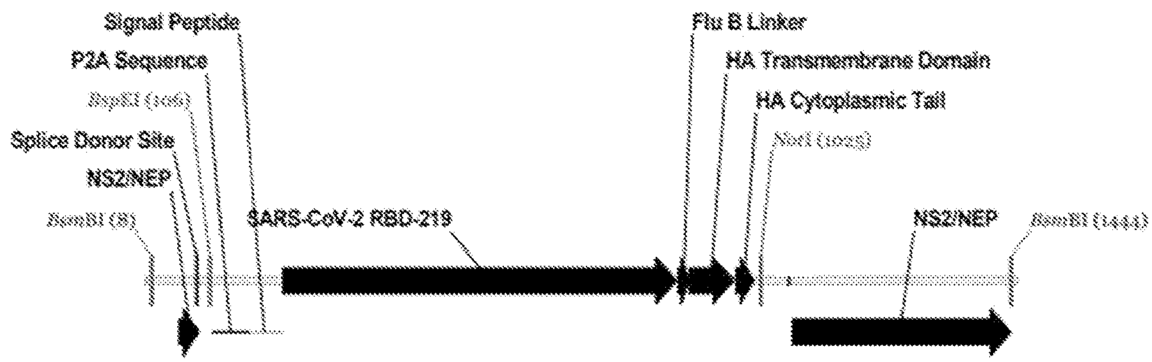
Figure 1:
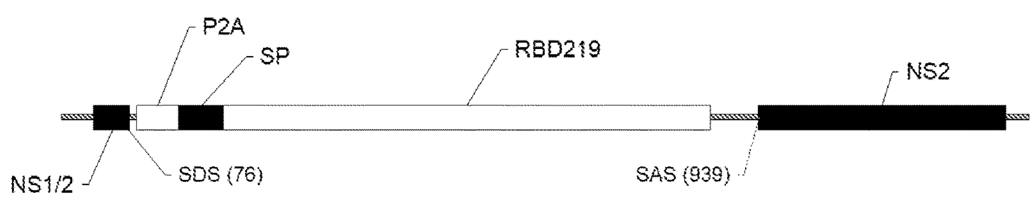

Specification includes a Sequence Listing.

(56) References Cited

OTHER PUBLICATIONS

Jin, H et al. "Influenza virus hemagglutinin and neuraminidase cytoplasmic tails control particle shape", 1997, Embo J., vol. 16, No. 6, pp. 1236-1247.
Kida, H et al. "Inhibition of Virus=Induced Hemolysis with Monoclonal Antibodies to Different Antigenic Areas on the Hemagglutinin Molecule of A/Seal/Massachusetts/1/80 (H 7N 7) Influenza Virus" , Arch Virol., 1983, vol. 76, No. 2, pp. 91-99.
Kilbourne, E D, "Comparative Efficacy of Neuraminidase-Specific and Conventional Influenza Virus Vaccines in Induction of Antibody to Neuraminidase in Humans", 1976, Infect Dis., vol. 134, No. 4, pp. 384-394.
Kirkpatrick, E. et al. "The influenza virus hemagglutinin head evolves faster than the stalk domain", 2018, Scientific Reports, 8:10432, 14 pages.
Krystal, M et al. "Evolution of influenza A and B viruses: Conservation of structural features in the hemagglutinin genes", PNAS, 1982; vol. 79, pp. 4800-4804.
Loes, A N et al. "Attenuated influenza virions expressing the SARS-CCoV-2 receptor-binding domain induce neutralizing antibodies in mice", bioRxiv, Sep. 3, 2020, https://doi.org/10.1101/2020.08.12.248823, 12 pgs.
Mcauley, J L et al. "Influenza Virus Neuraminidase Structure and Functions", 2019, Front Microbiol., vol. 10, article 39, doi: 10.3389/fmicb.2019.00039, 13 pgs.
Mintaev, R R et al. "Co-evolution analysis to predict protein-protein interactions within influenza virus envelope", 2014, J. Bioinforma. Comput. Biol., vol. 12, No. 2, pp. 1441008.
Mitnaul, L J et al. "The Cytoplasmic Tail of Influenza A Virus Neuraminidase (NA) Affects NA Incorporation into Virions, Virion Morphology, and Virulence in Mice but Is Not Essential for Virus Replication", 1996, J. Virol., vol. 70, No. 2, pp. 873-879.
Morokutti, A et al. "Intranasal vaccination with a replication-deficient influenza virus induces heterosubtypic neutralising mucosal IgA antibodies in humans", 2014, Vaccine, vol. 32, No. 17, pp. 1897-1900.
Moules, V et al. "In vitro characterization of naturally occurring influenza H3NA-viruses lacking the NA gene segment: Toward a new mechanism of viral resistance?", 2010, Virology, vol. 404, No. 2, pp. 215-224.
Mueller, S N et al. "Immunization with Live Attenuated Influenza Viruses That Express Altered NS1 Proteins Results in Potent and Protective Memory CD8+ T-Cell Responses", J Virol., 2010, vol. 84, No. 4, pp. 1847-1855.
Nemeroff, M E et al. "Identification of cis-Acting Intron and Exon Regions in Influenza Virus NS1 mRNA That Inhibit Splicing and Cause the Formation of Aberrantly Sedimenting Presplicing Complexes", 1992, Mol. Cell. Biol., vol. 12, No. 3, pp. 962-970.
Nicolodi, C et al. "Safety and immunogenicity of a replication-deficient H5N1 influenza virus vaccine lacking NS1", 2019, Vaccine, vol. 37, No. 28, pp. 3722-3729.
Plotch, S J et al. "In vitro splicing of influenza viral NS1 mRNA and NS1-β-globin chimeras: Possible mechanisms for the control of viral mRNA splicing", 1986, PNAS, vol. 83, No. 15, pp. 5444-5448.
Varghese, J N et al. "Structure of the influenza viruso glycoprotein antigen neuraminidase at 2.9 A resolution", 1983, Nature, vol. 303, pp. 35-40.
Wachek, V et al. "A Novel Type of Influenza Vaccine: Safety and Immunogenicity of Replication-Deficient Influenza Virus Created by Deletion of the Interferon Antagonist NS1 ", J. Infect. Dis., 2010, vol. 201, No. 3, pp. 354-362.
Wang, Pui et al. "Generation of DeINS1 Influenza Viruses: a Strategy for Optimizing Live Attenuated Influenza Vaccines", mBio, 2019, vol. 10, issue 5, e02180-19.
Wang, T T et al. "Broadly Protective Monoclonal Antibodies against H3 Influenza Viruses following Sequential Immunization with Different Hemagglutinins", PLoS Pathog., 2010, vol. 6, No. 2, e1000796.
Ward, C W et al. "The disulphide bonds of an Asian influenza virus neuraminidase", 1983, FEBS Lett., vol. 153, No. 1, pp. 29-33.
Van Wielink, R et al. "Mutations in the M-Gene Segment Can Substantially Increase Replication Efficiency of NS 1 Deletion Influenza A Virus in MDCK Cells", J of Virology, 2012, vol. 86, No. 22, p. 12341-12350.
Wiley, D C et al. "Structural identification of the antibody-binding sites of Hong Kong influenza haemagglutinin and their involvement in antigenic variation", 1981, Nature, vol. 289, No. 5796, pp. 373-378.
Yasugi, M et al. "Human Monoclonal Antibodies Broadly Neutralizing against Influenza B Virus", 2013, PLoS Pathog., vol. 9, issue 2, e10031.
International Search Report for corresponding International Patent Application No. PCT/US2021/059788, dated Apr. 13, 2022.

a.

BGHB delNS-RBD219 BSMBI spm1
1325 bp b.

BGHB delNS-RBD219 BSMBI spm1 plus generic Linker, TM Domain and CT Codon Opt
1460 bp c.

BGHB delNS-RBD219 BSMBI spm1 plus HA2 Linker, TM Domain and CT Codon Opt
1454 bp d.

BdelNS-RBD219
1304 bp

Western Blot – D19 Murmansk Supernatant (60S exposure, R&D Mouse Anti-RDB)

| | Virus | Sample | RBD Concentration (ng) * |
|---|---|---|---|
| **1** | 40ng RBD Antigen | | 40.0 |
| **2** | Murmansk B1 P2 | MOI 5 | 9.6 |
| **3** | Murmansk B1 HG P2 | MOI 5 | 34.1 |
| **4** | Murmansk B3 P2 | MOI 5 | 25.3 |
| **5** | Murmansk B3 HG P2 | MOI 5 | 3.6 |

*Based off of ImageLab Quantitative software, measuring band intensity relative to the antigen control. 30S exposure image used.

B/Florida D-19 B1 NS Identity

One Step RT-PCR

| Passage | P0 | P1 | P2 | P3 | P4 | P5 | P6 | P7 |
|---|---|---|---|---|---|---|---|---|
| **NP titer** (Log10 FFU/ml) | 6.97 | 6.24 | 7.14 | 7.15 | 6.95 | 7.03 | 6.94 | 7.09 |
| **RBD Titer** (Log10 FFU/ml) | 6.78 | 6.04 | 6.92 | 6.94 | 6.71 | 6.88 | 6.64 | 6.81 |

B/Murmansk D-19 B1 NS Identity

One Step RT-PCR

| Passage | P0 | P1 | P2 | P3 | P4 | P5 | P6 | P7 |
|---|---|---|---|---|---|---|---|---|
| **NP titer** (Log10 FFU/ml) | 6.72 | 7.50 | 7.69 | 7.51 | 7.69 | 7.79 | 7.77 | 7.99 |
| **RBD Titer** (Log10 FFU/ml) | 6.77 | 7.32 | 7.47 | 7.25 | 7.49 | 7.60 | 6.43 | 6.37 |

a.

Fig. 5

Wuhan-Hu-1/2019 Reference strain (GenBank MN908947)

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTNGVGYQPYRVVVLSFELLHAPATVCGPKKSTNLVKNKCVNFNFNGLTGT (SEQ ID NO:1)

hCoV-19/Austria/CeMM0639/2020 (EPI_ISL_475936)

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTNGVGYQPYRVVVLSFELLHAPATVCGPKKSTNLVKNKCVNFNFNGLTGT (SEQ ID NO:2)

hCoV-19/Sweden/20-51988/2020 (EPI_ISL_4755690)

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTNGVGYQPYRVVVLSFELLHAPATVCGPKKSTNLVKNKCVNFNFNGLTGT (SEQ ID NO:3)

hCoV-19/Singapore/397/2020 (EPI_ISL_469146)

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTNGVGYQPYRVVVLSFELLHAPATVCGPKKSTNLVKNKCVNFNFNGLTGT (SEQ ID NO:4)

Fig. 5 (continued)

hCoV-19/USA/IL-NM0118/2020 (EPI_ISL_444601)

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTNGVGYQPYRVVVLSFELLHAPATV (SEQ ID NO:5)

SARS CoV-2 RBD amino acid sequence inserted (RBD219, see scheme in Fig.1)

NITNLCPFGEVFNATRFASVYAWNRKRISNCVADYSVLYNSASFSTFKCYGVSPTKLN DLCFTNVYADSFVIRGDEVRQIAPGQTGKIADYNYKLPDDFTGCVIAWNSNNLDSKVG GNYNYLYRLFRKSNLKPFERDISTEIYQAGSTPCNGVEGFNCYFPLQSYGFQPTNGV GYQPYRVVVLSFELLHAPATVCGPKKSTNLVKNKCVNFNFNGLTGT (SEQ ID NO:6)

SARS-CoV-2 RBD-219 Original Sequence

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTNGVGYQPYRVVVLSFELLHAPATV (SEQ ID NO:54)

SARS-CoV-2 RBD-219 Original Sequence: England Variant: N501Y

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQ PTYGVGYQPYRVVVLSFELLHAPATV (SEQ ID NO:55)

SARS-CoV-2 RBD-219 Original Sequence: South Africa Variant: K417N, E484K and N501Y

NITNLCPFGEVFNATRFASVYAWNRKRISNCVADYSVLYNSASFSTFKCYGVS PTKLNDLCFTNVYADSFVIRGDEVRQIAPGQTGNIADYNYKLPDDFTGCVIAWNSNNL DSKVGGNYNYLYRLFRKSNLKPFERDISTEIYQAGSTPCNGVKGFNCYFPLQSYGFQ PTYGVGYQPYRVVVLSFELLHAPATV (SEQ ID NO:56)

Fig. 5 (continued)

SARS-CoV-2 RBD-219 Delta Variant: L452R and T478K

NITNLCPFGEVFNATRFASVYAWNRKRISNCVADYSVLYNSASFSTFKCYGVS PTKLNDLCFTNVYADSFVIRGDEVRQIAPGQTGKIADYNYKLPDDFTGCVIAWNSNNL DSKVGGNYNYRYRLFRKSNLKPFERDISTEIYQAGSKPCNGVEGFNCYFPLQSYGFQ PTNGVGYQPYRVVVLSFELLHAPATV (SEQ ID NO:57)

Codon optimized NS construct nucleotide sequence:

BGHB delNS-RBD219 BSMBI spm1

(CGTCTCAGGG)AGCAGAAGCAGAGGATTTGTTTAGTCACTGGCAAACAGG AAAAATGGCGGACAATATGACCACAACACAAATTGAGGT*GG*GTCCGGGAGCAGG ATCCGGAGCAACAAATTTCTCACTTCTTAAACAAGCAGGGGACGTGGAAGAAAAT CCAGGACCAATGAAAACAGATACACTTCTTCTTTGGGTGCTGCTTTTGTGGGTTCC AAGATCACATGGGAATATCACGAATCTGTGCCCCTTTGGAGAGGTGTTCAATGC TACCCGCTTTGCTTCAGTGTACGCTTGGAATAGGAAACGGATCAGTAATTGCGT GGCTGATTATTCTGTGCTGTACAATAGCGCAAGCTTCAGCACATTCAAATGCTAT GGAGTGAGCCCCACAAAACTGAATGATCTGTGCTTCACTAATGTTTACGCCGAT TCATTTGTGATACGCGGAGATGAGGTGAGACAGATTGCCCCTGGCCAAACAGG AAAAATCGCGGATTACAATTACAAACTGCCAGATGATTTCACTGGATGCGTGAT TGCATGGAATTCAAATAATCTGGATAGTAAAGTTGGAGGCAATTACAATTACCT GTACAGACTGTTCAGAAAAAGCAATCTGAAACCCTTTGAGCGAGATATCAGCAC CGAAATCTACCAGGCTGGCTCTACGCCTTGCAATGGAGTGGAGGGATTCAATTG TTATTTTCCTCTGCAGAGTTACGGATTCCAACCGACCAATGGTGTGGGATATCA GCCCTACAGAGTGGTGGTGCTGAGCTTCGAACTGCTTCACGCTCCAGCAACAGT GTGCGGACCCAAAAAATCTACTAATCTGGTGAAAAATAAGTGCGTGAATTTCAA TTTCAATGGACTGACGGGAACGTAATGATGAGCGGCCGCCCAAGCAGAAAGTGG TACTAACCTTCTTCTCTTTCTTCTCCTGACAGTGGAGGATGAAGAAGATGGCCATC GGATCCTCAATTCACTCTTCGAGCGTCTTAATGAAGGACATTCAAAGCCAATTCGA GCAGCTGAAACTGCGGTGGGAGTCTTATCCCAATTTGGTCAAGAGCACCGATTAT CACCAGAAGAGGGAGACAATTAGACTGGTCACGGAAGAACTTTATCTTTTAAGTA AAAGAATTGATGATAACATATTGTTCCACAAAACAGTAATAGCTAACAGCTCCATA ATAGCTGACATGGTTGTATCATTATCATTATTAGAAACATTGTATGAAATGAAGGAT GTGGTTGAAGTGTACAGCAGGCAGTGCTTGTGAATTTAAAATAAAAATCCTCTTGT TACTACT(AATAC*GAGACG)* (nucleic acids in brackets are for cloning, SEQ ID NO:7)

Fig. 5 (continued)

B/Thüringen/02/06 amino acid sequence PB1 D67N:

MNINPYFLFIDVPIQAAISTTFPYTGVPPYSHGTGTGYTIDTVIRTHEYSNKGKQ YVSDITGCTMInPTNGPLPEDNEPSAYAQLDCVLEALDRMDEEHPGLFQAASQNAME ALMVTTVDKLTQGRQTFDWTVCRNQPAATALNTTITSFRLNDLNGADKGGLVPFCQD IIDSLDKPEMTFFSVKNIKKKLPAKNRKGFLIKRIPMKVKDRISRVEYIKRALSLNTMTKD AERGKLKRRAIATAGIQIRGFVLVVENLAKNICENLEQSGLPVGGNEKKAKLSNAVAK MLSNCPPGGISMTVTGDNTKWNECLNPRIFLAMTERITRDSPIWFRDFCSIAPVLFSN KIARLGKGFMITSKTKRLKAQIPCPDLFSIPLERYNEETRAKLKRLKPFFNEEGTASLSP GMMMGMFNMLSTVLGVAALGIKNIGNKEYLWDGLQSSDDFALFVNAKDEETCMEGI NDFYRTCKLLGINMSKKKSYCNETGMFEFTSMFYRDGFVSNFAMEIPSFGVAGVNES ADMAIGMTIIKNNMINNGMGPATAQTAIQLFIADYRYTYKCHRGDSKVEGKRMKIIKEL WENTKGRDGLLVADGGPNIYNLRNLHIPEIVLKYNLMDPEYKGRLLHPQNPFVGHLSI EGIKEADITPAHGPVRKMDYDAVSGTHSWRTKRNRSILNTDQRNMILEEQCYAKCCN LFEACFNSASYRKPVGQHSMLEAMAHRLRMDARLDYESGRMSKDDFEKAMAHLGEI GYT (SEQ ID No. 22)

B/Thüringen/02/06, amino acid sequence M1 K93R

MSLFGDTIAYLLSLTEDGEGKAELAEKLHCWFGGKEFDLDSALEWIKNKRCLT DIQKALIGASICFLKPKDQERKRRFITEPLSGMGTTATKrKGLILAERKMRKCVSFHEAF EIAEGHESSALLYCLMVMYLNPGNYSMQVKLGTLCALCEKQASHSHRAHSRAARSS VPGVRREMQMVSAMNTAKTMNGMGKGEDVQKLAEELQSNIGVLRSLGASQKNGEG IAKDVMEVLKQSSMGNSALVKKYL (SEQ ID No. 23)

B/Thüringen/02/06 BGHB ∆NS, amino acid sequence NS2 Y117H

MADNMTTTQIEWRMKKMAIGSSIHSSSVLMKDIQSQFEQLKLRWESYPNLVKS TDYHQKRETIRLVTEELYLLSKRIDDNILFHKTVIANSSIIADMVVSLSLLETLYEMKDVV EVhSR (SEQ ID No. 24)

Fig. 5 (continued)

Influenza B/Thueringen/02/06 wild-type NS segment nucleotide sequence

AGCAGAAGCAGAGGATTTGTTTAGTCACTGGCAAACAGGAAAAATGGCGGACAAT
ATGACCACAACACAAATTGAGGTGGGTCCGGGAGCAACCAATGCCACCATAAACT
TTGAAGCAGGAATTCTGGAGTGCTATGAAAGACTTTCATGGCAAAGGGCCCTTGA
CTACCCTGGTCAAGACCGCCTAAACAGACTAAAGAGAAAATTAGAGTCAAGAATA
AAGACTCACAACAAAAGTGAGCCTGAAAGTAAAAGGATGTCTCTTGAAGAGAGAA
AAGCAATTGGAGTAAAAATGATGAAAGTACTCCTATTTATGAATCCGTCTGCTGGA
ATTGAAGGGTTTGAGCCATACTGTATGAAAAGTTCCTCAAAGAGCAACTGTCCGA
AATACAATTGGATCGATTACCCTTCAACCCCAGGGAGGTGCCTTGATGACATAGA
AGAAGAACCAGATGATGTTGATGGCCCAACTGAAATAGTATTAAGGGACATGAAC
AACAAAGATGCAAGGCAAAAGATAAAGGAGGAAGTAAACACTCAGAAAGAAGGGA
AGTTCCGTTTGACAATAAAAAGGGATATGCGTAATGTATTGTCCCTGAGAGTGTTA
GTAAACGGAACATTCCTCAAACACCCCAATGGGTACAAGTCCTTATCAACTCTGCA
TAGATTGAATGCATATGACCAGAGTGGAAGGCTTGTTGCTAAACTTGTTGCTACTG
ATGATCTTACAGTGGAGGATGAAGAAGATGGCCATCGGATCCTCAATTCACTCTT
CGAGCGTCTTAATGAAGGACATTCAAAGCCAATTCGAGCAGCTGAAACTGCGGTG
GGAGTCTTATCCCAATTTGGTCAAGAGCACCGATTATCACCAGAAGAGGGAGACA
ATTAGACTGGTCACGGAAGAACTTTATCTTTTAAGTAAAAGAATTGATGATAACATA
TTGTTCCACAAAACAGTAATAGCTAACAGCTCCATAATAGCTGACATGGTTGTATC
ATTATCATTATTAGAAACATTGTATGAAATGAAGGATGTGGTTGAAGTGTACAGCA
GGCAGTGCTTGTGAATTTAAAATAAAAATCCTCTTGTTACTACT (SEQ ID No. 16)

Influenza B Thueringen/02/06 wild-type NS1 amino acid sequence
MADNMTTTQIEVGPGATNATINFEAGILECYERLSWQRALDYPGQDRLNRLKRKLES
RIKTHNKSEPESKRMSLEERKAIGVKMMKVLLFMNPSAGIEGFEPYCMKSSSKSNCP
KYNWIDYPSTPGRCLDDIEEEPDDVDGPTEIVLRDMNNKDARQKIKEEVNTQKEGKF
RLTIKRDMRNVLSLRVLVNGTFLKHPNGYKSLSTLHRLNAYDQSGRLVAKLVATDDLT
VEDEEDGHRILNSLFERLNEGHSKPIRAAETAVGVLSQFGQEHRLSPEEGDN (SEQ
ID No. 20)

Fig. 5 (continued)

Influenza B Thueringen/02/06 wild-type NEP/NS2 amino acid sequence

MADNMTTTQIEWRMKKMAIGSSIHSSSVLMKDIQSQFEQLKLRWESYPNLVKSTDYH
QKRETIRLVTEELYLLSKRIDDNILFHKTVIANSSIIADMVVSLSLLETLYEMKDVVEVYS
RQCL (SEQ ID No. 50)

Influenza A/Puerto Rico/8/34 wild-type NS segment nucleotide sequence

AGCAAAAGCAGGGTGACAAAGACATAATGGATCCAAACACTGTGTCAAGCTTTCA
GGTAGATTGCTTTCTTTGGCATGTCCGCAAACGAGTTGCAGACCAAGAACTAGGT
GATGCCCCATTCCTTGATCGGCTTCGCCGAGATCAGAAATCCCTAAGAGGAAGG
GGCAGCACCCTCGGTCTGGACATCGAGACAGCCACACGTGCTGGAAAGCAGATA
GTGGAGCGGATTCTGAAAGAAGAATCCGATGAGGCACTTAAAATGACCATGGCCT
CTGTACCTGCGTCGCGTTACCTAACTGACATGACTCTTGAGGAAATGTCAAGGGA
CTGGTCCATGCTCATACCCAAGCAGAAAGTGGCAGGCCCTCTTTGTATCAGAATG
GACCAGGCGATCATGGATAAGAACATCATACTGAAAGCGAACTTCAGTGTGATTT
TTGACCGGCTGGAGACTCTAATATTGCTAAGGGCTTTCACCGAAGAGGGAGCAAT
TGTTGGCGAAATTTCACCATTGCCTTCTCTTCCAGGACATACTGCTGAGGATGTCA
AAAATGCAGTTGGAGTCCTCATCGGGGGACTTGAATGGAATGATAACACAGTTCG
AGTCTCTGAAACTCTACAGAGATTCGCTTGGAGAAGCAGTAATGAGAATGGGAGA
CCTCCACTCACTCCAAAACAGAAACGAGAAATGGCGGGAACAATTAGGTCAGAAG
TTTGAAGAAATAAGATGGTTGATTGAAGAAGTGAGACACAAACTGAAGATAACAGA
GAATAGTTTTGAGCAAATAACATTTATGCAAGCCTTACATCTATTGCTTGAAGTGG
AGCAAGAGATAAGAACTTTCTCGTTTCAGCTTATTTAATAATAAAAAACACCCTTGT
TTCTACT (SEQ ID No. 51)

Influenza A/Puerto Rico/8/34 wild-type NS1 amino acid sequence

MDPNTVSSFQVDCFLWHVRKRVADQELGDAPFLDRLRRDQKSLRGRGSTLGLDIET
ATRAGKQIVERILKEESDEALKMTMASVPASRYLTDMTLEEMSRDWSMLIPKQKVAG
PLCIRMDQAIMDKNIILKANFSVIFDRLETLILLRAFTEEGAIVGEISPLPSLPGHTAEDVK
NAVGVLIGGLEWNDNTVRVSETLQRFAWRSSNENGRPPLTPKQKREMAGTIRSEV
(SEQ ID No. 52)

Fig. 5 (continued)

Influenza A/Puerto Rico/8/34 wild-type NEP/NS2 amino acid sequence
MDPNTVSSFQDILLRMSKMQLESSSGDLNGMITQFESLKLYRDSLGEAVMRMGDLH
SLQNRNEKWREQLGQKFEEIRWLIEEVRHKLKITENSFEQITFMQALHLLLEVEQEIRT
FSFQLI (SEQ ID No. 53)

INFLUENZA VIRUS ENCODING A TRUNCATED NS1 PROTEIN AND A SARS-COV RECEPTOR BINDING DOMAIN

CROSS-REFERENCE TO RELATED APPLICATIONS

This application is the U.S. national stage of International Patent Application No. PCT/US2021/059788, filed on Nov. 17, 2021, which claims the benefit of priority under 35 U.S.C. § 119(e) from U.S. Patent Application No. 63/114,941, filed on Nov. 17, 2020. The disclosures of the foregoing applications are incorporated herein by reference in their entirety.

SEQUENCE LISTING

The entire content of a Sequence Listing titled "Sequence_Listing.txt," created on Jun. 8, 2023 and having a size of 68 kilobytes, which has been submitted in electronic form in connection with the present application, is hereby incorporated by reference herein in its entirety.

FIELD OF THE INVENTION

The present invention refers to a recombinant influenza virus encoding a fusion protein comprising a truncated NS1 protein and a SARS-CoV receptor binding domain and its use for prophylactic treatment, a pharmaceutical preparation comprising said virus for use in prime boost vaccination and a two-component vaccine for prime boost vaccination.

BACKGROUND OF THE INVENTION

The emergence of newly identified viruses highlights the need for the development of novel antiviral strategies. Severe acute respiratory syndrome coronavirus 2 (SARS-CoV-2) is a newly emerged coronavirus which causes a severe acute respiratory disease, COVID-19. COVID-19 first appeared in Wuhan, a city in China, in December 2019. SARS-CoV is an animal virus, perhaps bats are the reservoir of the virus, which spread to other animals including humans. The transmission of SARS-CoV is primarily from human to human. These viruses generally target the respiratory system of a patient and lead to influenza-like symptoms.

As of Oct. 30, 2020, the World Health Organization has reported about 45 million confirmed cases worldwide, resulting in 1.18 million deaths.

Symptoms of COVID-19 can range from mild-illness to pneumonia, renal dysfunction, respiratory and multi-organ failure. Unlike the previous SARS-CoV, COVID-19 has proved to be more lethal. Patients infected with COVID-19 rely on their natural immunity and generally seek supportive care to help relieve symptoms. In severe cases, treatment involves mechanical ventilation and vital organ function support.

Thus far, there has been no vaccine or therapeutic agent to prevent or successfully treat SARS-CoV-2 infection. In view of the continuing threat to human health, there is an urgent need for preventive and therapeutic antiviral therapies for SARS-CoV-2 control.

Thus, there is a need for a composition for the prevention of SARS-CoV infections and their associated complications.

SUMMARY OF THE INVENTION

It is the objective of the present invention to provide a composition for preventing SARS-CoV infections.

The objective is solved by the subject matter of the present invention.

The present invention discloses a recombinant influenza virus comprising a modified NS segment, encoding a) a fusion protein comprising from its N to C-terminus
   - a truncated NS1 protein consisting of 10 to 20 amino acids of the N-terminus of the respective wild type NS1 protein,
   - optionally a linker sequence,
   - optionally a 2A self-cleaving peptide, specifically a P2A sequence,
   - a signal peptide,
   - a SARS-CoV receptor binding domain, optionally comprising about 10 to 50 additional amino acids of the SARS-CoV S1 subunit at its C-terminus, and b) an NS2 protein.

Specifically, the present invention provides an isolated fusion protein comprising from its N to C-terminus

- a truncated NS1 protein consisting of 10 to 20 amino acids of the N-terminus of the respective wild type NS1 protein,
- optionally a linker sequence,
- optionally a 2A self-cleaving peptide, specifically a P2A sequence,
- a signal peptide, and
- a SARS-CoV receptor binding domain containing the receptor binding motif (RBM), optionally comprising about 10 to 50 additional amino acids of the SARS-CoV 51 subunit at its C-terminus, optionally fused to a transmembrane domain.

Specifically, the SARS-CoV receptor binding domain is SARS-CoV-2 receptor binding domain.

Specifically, the recombinant influenza virus encoding the fusion protein and NS2 protein (NS1-SARS-CoV-2RBD/NS2) is a live attenuated influenza virus. Influenza virus attenuated live vaccines based on reverse genetics technology of influenza virus have been shown to be safe and effective, also when expressing foreign genes. However, life attenuated influenza virus expressing SARS-CoV2 RBD as part of a fusion protein has not been reported. Major obstacles in this connection are lack of stability of the chimeric NS1 gene, insufficient expression of the inserted antigen and that replication of the chimeric virus is affected by the chimeric NS1 gene. Said obstacles are overcome by the present invention.

Specifically, the recombinant influenza virus is an influenza B virus, specifically a human influenza B virus.

Vaccine candidates against SARS-CoV-2 based on the RBD are under development, however, in contrast to all other approaches, expression of the RBD by an influenza virus would permit to immunize and protect against influenza and Covid-19 at the same time. Moreover, intranasal application would allow to induce mucosal immunity with the potential to block and eliminate the virus directly at the site of entry of the virus. Thus induction of sterilizing immunity would be feasible. In contrast to other approaches which usually do not provide mucosal immunity, this immunization route has the potential not only to protect from disease but also from infection. The expression of the RBD is achieved by influenza viruses, specifically influenza B viruses, which grow to high titers in tissue culture, an important prerequisite for industrial production of viral vaccine vectors.

According to an embodiment of the invention, the truncated NS1 protein comprises its N-terminal 10 to 18 amino acids, specifically the NS1 protein comprises up to 16 amino acids.

According to an embodiment, the recombinant influenza virus further comprises up to 40, specifically up to 30, specifically up to 27 amino acids of the SARS-CoV S1 subunit C-terminal of the RBD.

According to a specific embodiment, the recombinant influenza virus described herein comprises SEQ ID NOs. 1-6 or 54-57.

According to an embodiment, there is a linker between the NS1 fragment and the encoding 2A cleavage peptide and/or the signal peptide, specifically having a length of 2 to 10 amino acids. Specifically, the linker sequence comprises glycine, alanine and/or serine residues.

According to a further specific embodiment, the recombinant influenza virus comprises modifications of the NA and/or HA proteins.

Herein provided is also the recombinant influenza virus described herein for use in the preparation of a medicament for prophylactic treatment of a disease condition caused by or associated with an infection by a coronavirus and/or an influenza virus specifically inducing immunity against a coronavirus and/or an influenza virus.

Further provided is a pharmaceutical formulation such as a vaccine, comprising the recombinant influenza virus encoding NS1-SARS-CoV-2-RBD/NS2 as described herein in an effective amount.

Further provided herein is a pharmaceutical formulation comprising the recombinant influenza virus, and a physiologically acceptable excipient.

Specifically, the pharmaceutical preparation is for inducing immunity to prevent infection and/or disease by a coronavirus and/or influenza virus, wherein the effective amount is effective in inducing immunity for preventing infection of susceptible cells by the virus.

Specifically, the pharmaceutical preparation is formulated for local administration, preferably for application to the upper and lower respiratory tract, nasal, pulmonary, intraoral, ocular, or dermal use, or for systemic administration, preferably for parenteral administration.

Specifically, the pharmaceutical preparation is administered to a subject as a spray, a powder, a gel, an ointment, a cream, a foam, or a liquid solution, a lotion, a patch, a gargle solution, an aerosolized powder, an aerosolized liquid formulation, granules, capsules, specifically comprising a preparation for parenteral administration.

Specifically, the coronavirus is a β-coronavirus, preferably selected from the group consisting of SARS-CoV-2, MERS-CoV, SARS-CoV-1, HCoV-0043, and HCoV-HKU1, or mutants thereof.

Specifically, the influenza virus is influenza A or B virus, more specifically it is influenza B virus.

Herein provided is also an isolated nucleic acid sequence expressing the recombinant influenza virus encoding NS1-SARS-CoV-2-RBD/NS2 as described herein. Specifically, the nucleic acid sequence comprises one or more artificial splice sites within the gene encoding the truncated NS1 protein.

According to a further embodiment of the invention, a two-component vaccine is provided herein, comprising the recombinant influenza virus encoding NS1-SARS-CoV-2RBD/NS2 as described herein with native hemagglutinin (HA) from Victoria or Yamagata lineages, for use in the vaccination of a subject, wherein a priming composition, comprising one, two or three recombinant influenza virus strains comprising the NS1-SARS-CoV-2-RBD fusion protein described herein, is formulated for prime-administration prior to a boosting composition, comprising one, two or three recombinant influenza virus strains comprising the NS1-SARS-CoV-2-RBD fusion protein in the priming composition but antigenically differing in the HA, formulated for boost-administration. Specifically, the HA head is antigenically different.

According to an embodiment, the boosting composition is administered 2 to 8 weeks after the priming composition, specifically 2, 3, 4, 5, 6, 7, or 8 weeks after the priming composition.

According to an alternative embodiment, the boosting composition is administered about 3 weeks after the priming composition.

According to a specific embodiment, the recombinant influenza virus of the priming composition, encoding the NS1-SARS-CoV-2-RBD fusion protein, comprises a native HA with a B/Victoria derived HA, and the recombinant influenza virus of the boosting composition, also comprising the NS1-SARS-CoV-2-RBD fusion protein, comprises a native HA with a B/Yamagata lineage HA, or wherein the recombinant influenza virus of the priming composition comprises a native HA with a B/Victoria lineage derived HA, and the recombinant influenza virus of the boosting composition comprises a native HA with a B/Yamagata lineage derived HA.

According to an embodiment, vaccination is for the prevention of corona virus related disease or infection and can further be simultaneously used for prevention of influenza virus infection.

Further provided herein is a kit for prime-boost vaccination comprising at least two vials, wherein a first vial contains a priming composition comprising one, two or three recombinant influenza virus strains comprising the NS1-SARS-CoV-2-RBD fusion protein, and a second vial contains a boosting composition comprising one, two or three delNS1 influenza virus strains of the same group as in the priming composition but with an antigenically different HA head.

FIGURES

FIG. 1: In silico design of the influenza B delNS-RBD219 segment. a) Soluble SARS-CoV-2 RBD in Influenza B Backbone (Delta-19) construct example. b) Anchored SARS-CoV-2 RBD in Influenza Backbone (Delta-19) with a generic linker to Influenza Hemagglutinin Transmembrane Domain and Cytoplasmic Tail construct. c) Anchored SARS-CoV-2 RBD in Influenza Backbone (Delta-19) with an Influenza B linker to Influenza Hemagglutinin Transmembrane Domain and Cytoplasmic Tail construct. d) In silico design of the influenza B delNS-RBD219 segment. General display.

Figure 2:
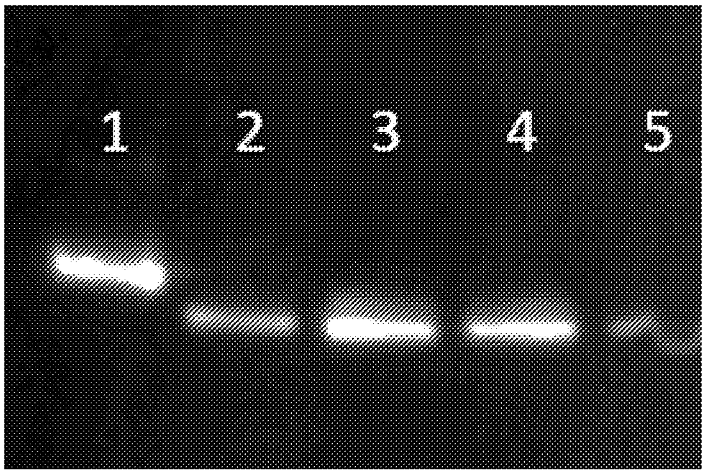

FIG. 2: SARS COV-2 protein expression is measured by western blot

Figure 3:
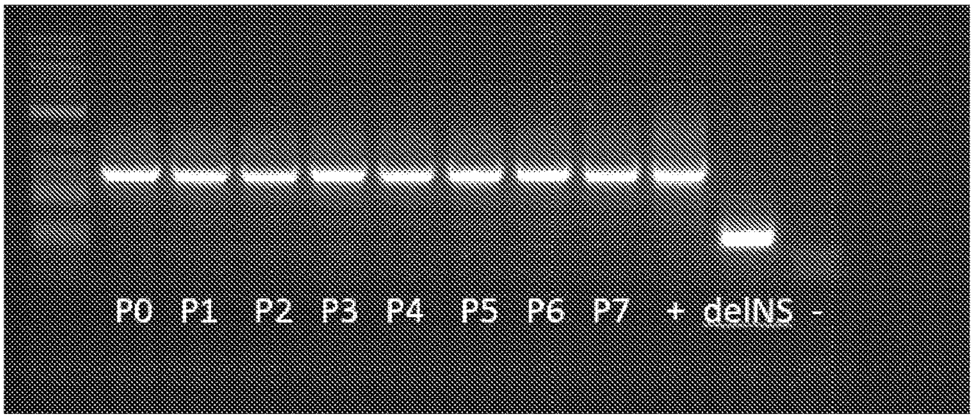
Figure 3:
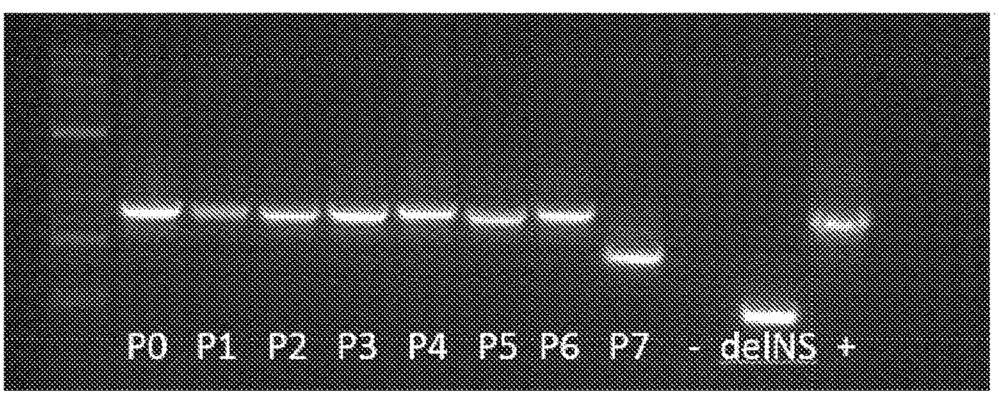

FIG. 3: NS gene sequence stability

Figure 4:
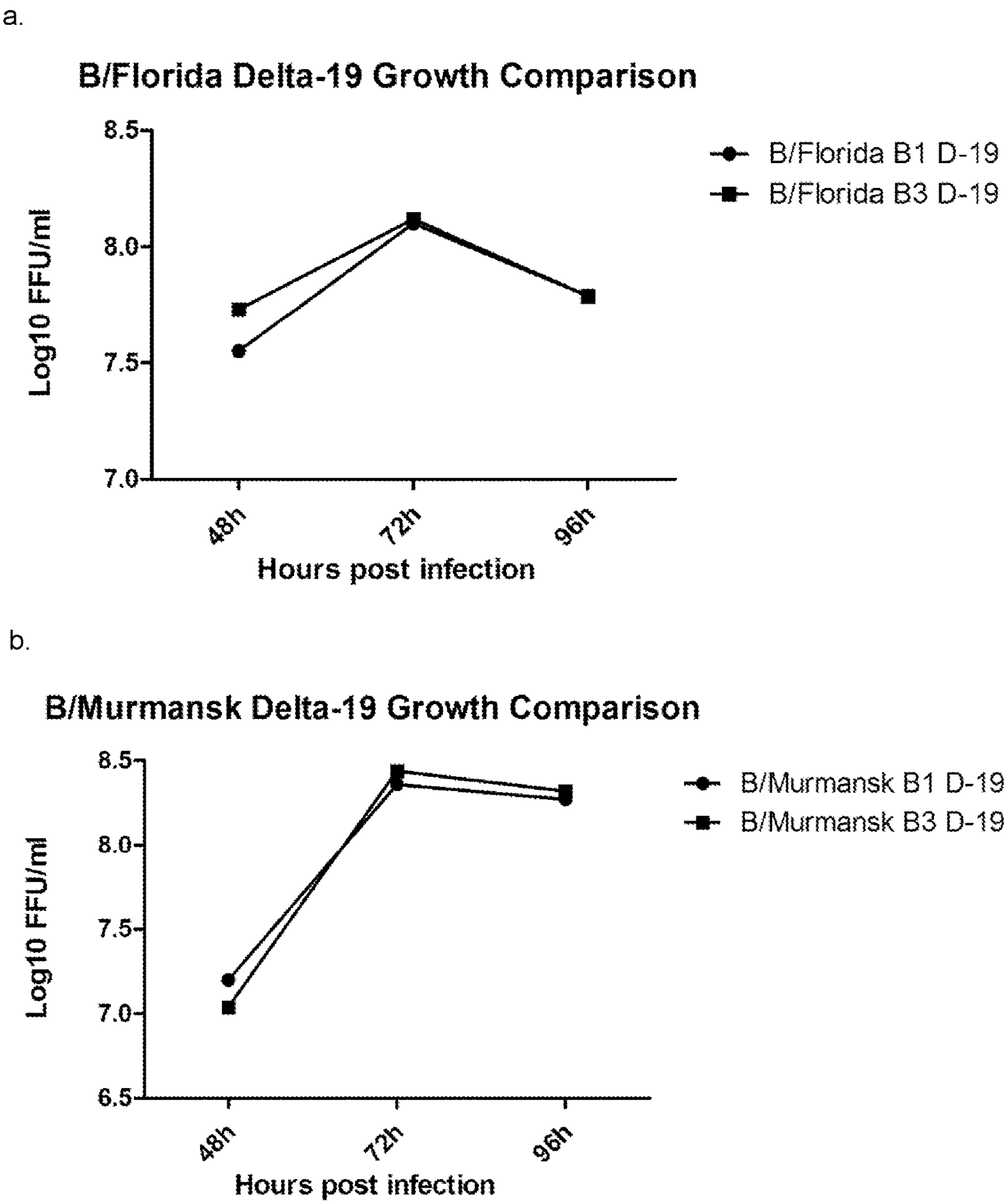

FIG. 4 *a*: B/Florida Delta-19 P7 growth curve on serum free Vero cells. *b*: B/Murmansk Delta-19 P4 Growth Curve on serum free Vero cells. Samples were collected at 28, 72 and 96 hours post infection and titered by multiplex FFA assay.

FIG. 5: Amino acid and nucleotide sequences

DETAILED DESCRIPTION

Unless indicated or defined otherwise, all terms used herein have their usual meaning in the art, which will be clear to the skilled person. Reference is for example made to the standard handbooks, such as Sambrook et al, "Molecular Cloning: A Laboratory Manual" (4th Ed.), Vols. 1-3, Cold Spring Harbor Laboratory Press (2012); Krebs et al., "Lewin's Genes XI", Jones & Bartlett Learning, (2017), and Murphy & Weaver, "Janeway's Immunobiology" (9th Ed., or more recent editions), Taylor & Francis Inc, 2017.

The subject matter of the claims specifically refers to artificial products or methods employing or producing such artificial products, which may be variants of native (wild-type) products. Though there can be a certain degree of sequence identity to the native structure, it is well understood that the materials, methods and uses of the invention, e.g., specifically referring to isolated nucleic acid sequences, amino acid sequences, fusion constructs, expression constructs, transformed host cells and modified proteins, are "man-made" or synthetic, and are therefore not considered as a result of "laws of nature".

The terms "comprise", "contain", "have" and "include" as used herein can be used synonymously and shall be understood as an open definition, allowing further members or parts or elements. "Consisting" is considered as a closest definition without further elements of the consisting definition feature. Thus "comprising" is broader and contains the "consisting" definition.

The term "about" as used herein refers to the same value or a value differing by +/−5% of the given value.

As used herein and in the claims, the singular form, for example "a", "an" and "the" includes the plural, unless the context clearly dictates otherwise.

As used herein, amino acids refer to twenty naturally occurring amino acids encoded by sixty-one triplet codons. These 20 amino acids can be split into those that have neutral charges, positive charges, and negative charges:

The "neutral" amino acids are shown below along with their respective three-letter and single-letter code and polarity: Alanine (Ala, nonpolar, neutral), Asparagine (Asn, N; polar, neutral), Cysteine (Cys, nonpolar, neutral), Glutamine (Gln, Q; polar, neutral), Glycine (Gly, nonpolar, neutral), Isoleucine (Ile, I; nonpolar, neutral), Leucine (Leu, L; nonpolar, neutral), Methionine (Met, M; nonpolar, neutral), Phenylalanine (Phe, nonpolar, neutral), Proline (Pro, P; nonpolar, neutral), Serine (Ser, S; polar, neutral), Threonine (Thr, T; polar, neutral), Tryptophan (Trp, W; nonpolar, neutral), Tyrosine (Tyr, Y; polar, neutral), Valine (Val, V; nonpolar, neutral), and Histidine (His, H; polar, positive (10%) neutral (90%)).

The "positively" charged amino acids are: Arginine (Arg, R; polar, positive), and Lysine (Lys, K; polar, positive).

The "negatively" charged amino acids are: Aspartic acid (Asp, ID, polar, negative), and Glutamic acid (Glu, E; polar, negative).

The influenza virion consists of an internal ribonucleoprotein core (a helical nucleocapsid) containing the single-stranded RNA genome, and an outer lipoprotein envelope lined inside by a matrix protein (M1). The segmented genome of influenza A and B virus consists of eight segments, seven for influenza C, of linear, negative polarity, single-stranded RNAs which encode eleven, some influenza A strains ten, polypeptides, including the RNA-dependent RNA polymerase proteins (PB2, PB1 and PA) and nucleoprotein (NP) which form the nucleocapsid; the matrix membrane proteins (M1, M2 or BM2 for influenza B, respectively); two surface glycoproteins which project from the lipid containing envelope: hemagglutinin (HA) and neuraminidase (NA); the nonstructural protein (NS1) and the nuclear export protein (NEP, also: NS2). Influenza B viruses encode also NB, a membrane protein which might have ion channel activity and most influenza A strains also encode an eleventh protein (PB1-F2) believed to have proapoptotic properties. Transcription and replication of the genome takes place in the nucleus and assembly occurs via budding on the plasma membrane. The viruses can reassort genes during mixed infections. Influenza virus adsorbs via HA to sialyloligosaccharides in cell membrane glycoproteins and glycolipids. Following endocytosis of the virion, a conformational change in the HA molecule occurs within the cellular endosome which facilitates membrane fusion, thus triggering uncoating. The nucleocapsid migrates to the nucleus where viral mRNA is transcribed. Viral mRNA is transcribed and processed by a unique mechanism in which viral endonuclease cleaves the capped 5'-terminus from cellular heterologous mRNAs which then serve as primers for transcription from viral RNA templates by the viral transcriptase. Transcripts terminate at sites 15 to 22 bases from the ends of their templates, where oligo(U) sequences act as signals for the addition of poly(A) tracts. Of the eight viral RNA molecules of influenza A virus so produced, six are monocistronic messages that are translated directly into the proteins representing HA, NA, NP and the viral polymerase proteins, PB2, PB1 and PA. The other two transcripts undergo splicing, each yielding two mRNAs which are translated in different reading frames to produce M1, M2, NS1 and NS2. In most of influenza A viruses, segment 2 also encodes for a second protein (PB1-F2), expressed from an overlapping reading frame. In other words, the eight viral RNA segments code for eleven proteins: nine structural and 2 non-structural (NS1, PB1-F2) proteins.

A "recombinant" virus is one which has been manipulated in vitro, e.g., using recombinant DNA techniques, to introduce changes to the viral genome, or otherwise artificially generated.

Through combining specific elements such as splice donor and acceptor sites a protease cleavage site and leader peptide with the RBD sequence, high levels of the RBD protein can be expressed and secreted out of the infected cells. This can be a further important prerequisite for inducing sufficient levels of neutralizing antibodies resulting in protection against infection with Sars-Covid-2.

Furthermore, according to a specific embodiment of this invention, the NS gene segment contains the natural splice donor and/or acceptor splice site. Alternatively, the sequences downstream of the splice donor and/or upstream of the acceptor site can be altered, preferably by introducing synthetic sequences in order to modify splicing activity. For example, it can be modified in that either the sequence surrounding the splice donor site is altered to increase the homology to the 5'end of the human U1 snRNA and/or the sequence upstream of the splice acceptor site containing the branch point is altered (Plotch and Krug, 1986, Nemeroff et al., 1992) and the pyrimidine stretch is replaced by a sequence that enhances splicing of the NS segment.

For example, the sequence surrounding the 5' splice site can be changed from*CAG/GTA* GATTG (SEQ ID NO:10, as found in the influenza A PR8 NS segment) to *CAG/GTAAGTAT* (SEQ ID NO:11) or *CAG/GTAAA* ATTG (SEQ ID NO:12, nucleotides complementary to the 5' end of the U1 snRNA are shown in bold italic letters, the splice donor site is indicated by "/").

For example, the sequence surrounding the 5' splice site can be changed from G*AG/GT* GG*GT* CC (SEQ ID NO:13, as found in the influenza B/Thueringen NS segment) to G *AG/GTA* GG*T* CC (SEQ ID NO:14, nucleotides complementary to the 5' end of the U1 snRNA are shown in bold italic letters, the splice donor site is indicated by "/").

In order to optimize splicing, the preferred synthetic acceptor site comprises a lariat consensus sequence and a pyrimidine stretch.

For example, the sequence upstream of the synthetic splice acceptor site can be as follows (SEQ ID NO: 15)
TACTAACCTTCTTCTCTTTCTTCTCCTGAC/AG.

The lariat consensus sequence is underlined, the pyrimidine stretch is bold, the splice acceptor site is indicated by "/".

In view of stability of the virus vector and the expression rate of the heterologous sequence it can be important to introduce the synthetic/modified sequence containing a lariat consensus sequence and a pyrimidine stretch at a specific position within the NS gene, e.g. directly upstream of the slice acceptor site.

Furthermore, it may be necessary to vary the distance between the lariat consensus sequence and the pyrimidine stretch to modify the splicing rate of the NS segment (Plotch S. and Krug R., 1986, Nemeroff M. et al., 1992).

The truncated NS1 protein of the herein described recombinant influenza virus consists of only about 10 to 20 amino acids of its N-terminus and thus the virus lacks a functional NS1 protein. It may be referred to it as delNS1 influenza virus. Deletion of the functional NS1 protein leads to a significant attenuation of influenza virus due to lack of replication in interferon competent cells or organisms (replication deficient phenotype). Viruses lacking the functional NS1 protein are not able to antagonize cytokine production of infected cells, therefore inducing self-adjuvanting and immune modulating effects. The hallmark of immune response after immunization with the inventive recombinant influenza virus is triggering of Th1 type of immune response associated with predominant IgG2A antibody isotype response (Ferko B. et al., 2004). The use of NS1 depleted influenza virus is highly advantageous due to increased T-cell response. Enhanced T-cell response may positively affect cross-reactivity of the HA stalk domain thus leading to increased memory effect of the cells and optimized vaccination effect. These improved T-cell responses are due to the release of interferon due to the lack of functional NS1 of the inventive virus comprising the NS1-SARS-CoV-2-RBD fusion protein.

Recall responses by memory cells was not only stronger but also appeared faster with delNS1 vaccine viruses. (Mueller et al, J Virol., 2010).

The lack of NS1 activity achieves highly advantageous properties for the life attenuated virus (LAIV). Specifically, when delivered intranasally, it infects cells of the upper respiratory tract and expresses viral antigens, but it does not form viral progeny and the vaccine strains are not shed by the recipient, making LAIV vaccines lacking functional NS1 protein very safe; and, additionally, since NS1 depleted strains are unable to counteract the host interferon (IFN) response, infection induces high levels of interferon, achieving a natural adjuvant effect that activates B and T cell-mediated immune responses.

Moreover, virus lacking functional NS1 protein stimulates cross-neutralizing serum antibodies against drift variants (Wachek V. et al., 2010), and cross-neutralizing mucosal IgA against different influenza A subtypes (Morokutti A. et al., 2014). Clinical data also indicate that pandemic deltaNS1 has potential for superior immunity (Nicolodi et al., 2019).

According to the invention, the term "replication deficient" is defined as replication rate in interferon competent host cells that is at least reduced by 95%, preferably 99%, preferably 99.9% compared to wild type influenza virus replication rate, determined by hemagglutination assay, TCID50 assay or plaque assay as well known in the art. Specifically, the influenza virus is completely replication deficient.

The influenza virus described herein can be human or animal influenza virus, such as, but not limited to, avian, equine, swine. Preferably, it is human influenza virus.

Specifically, the recombinant influenza virus encodes a fusion protein which comprises from its N to C-terminus a truncated NS1 protein consisting of 10 to 20 amino acids of the N-terminus of the respective wild type NS1 protein, a signal peptide, and a SARS-CoV receptor binding domain.

Specifically, the virus further comprises a full length NS2 protein.

Specifically, the truncated NS1 protein consists of 10, 11, 12, 13, 14, 15, 16, 17, 18, 19 or 20 amino acids of the N-terminus of the NS1-wt protein.

Coronaviruses are enveloped spherical particles, the spike glycoproteins (S protein) of which form a crown-like surface. The S protein consists of two subunits: S1 and S2. The fragment located in the middle of the S1 subunit (amino acids (aa) 318-510 with respect to the S1 subunit sequence) is the minimum receptor-binding domain (RBD) in SARS-CoV, which binds to the host cell receptor angiotensin converting enzyme 2 (ACE2). The RBD is about 192 amino acids long and comprises the receptor binding motif (RBM). The binding of RBD and ACE2 triggers the conformational change of the S2 subunit and virus particle invasion. The crystal structure of the RBD bound to ACE2 peptidase indicates that RBD presents a flat concave surface at the N-terminus of the receptor peptidase on which amino acids 445-460 anchor the entire receptor-binding loop of the RBD core This loop of about 70 amino acids (aa 424-494) makes complete contact with the ACE2 receptor and is called the receptor binding motif (RBM). Specifically, the RBD including the RBM comprises the sequence of any one of SEQ ID NOs:1 to 6 or 54-57 or is at least 95%, specifically 96, 97, 98, 99, 99.9% identical with SEQ ID NOs:1-6 or 54-57.

In an alternative embodiment, the RBD including the RBM comprises the sequence of any one of SEQ ID NOs:1 to 6 with 1, 2, 3, 4, or 5 amino acid substitutions, deletions or insertions.

The virus can encode the NS1-SARS-CoV-2-RBD fusion protein comprising additional 10 to 50 amino acids of the SARS-CoV S1 subunit linked to the C-terminus of RBD. Specifically, the RBD can comprise 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids (NS1-SARS-CoV-2-RBD-S1-fragment).

Specifically, the S1 subunit is of 27 amino acids.

Specifically, the fusion protein comprises SEQ ID NO:6 or SEQ ID NO:54, SEQ ID NO:55, SEQ ID NO:56 or SEQ ID NO:57.

The recombinant influenza virus encoding the NS1-SARS-CoV-2-RBD fusion protein can comprise one or more linker sequences of the same or different lengths, located between the truncated NS1 protein (NS1 fragment) and the 2A cleavage peptide and/or the signal peptide and/or the SARS-CoV receptor binding domain.

According to an embodiment, the linker has a length of 2 to 10 amino acids. Specifically, the linker sequence comprises glycine, serine and/or alanine residues. Specifically, the linker comprises at least one glycine and serine residue, more specifically the linker is GS, GSG, GGSGG (SEQ ID NO:17), GSGSG (SEQ ID NO:18), GSGSGSGS (SEQ ID NO:19), GG, GGG, or GGGG (SEQ ID NO:21). Preferably, the linker is a GSG linker.

According to a specific embodiment, the fusion protein also comprises a self-cleaving peptide, specifically located between the linker and the signal peptide. 2A self-cleaving peptides, or 2A peptides, is a class of 18-22 aa-long peptides, which can induce ribosomal skipping during translation of a protein in a cell. These peptides share a core sequence motif of DxExNPGP (SEQ ID NO:9), and are found in a wide range of viral families. They help generating polyproteins by causing the ribosome to fail at making a peptide bond.

Specifically, the peptide comprises the sequence ATNFSLLKQAGDVEENPGP (SEQ ID NO: 8).

The recombinant influenza virus encoding the NS1-SARS-CoV-2-RBD fusion protein was shown to be stable for at least 6 passages.

According to the embodiment of the present invention, the recombinant influenza virus disclosed herein is a reassortant virus, specifically wherein said virus comprises at least two gene segments of a seasonal or pandemic strain origin.

According to the invention, the recombinant influenza virus comprises modified hemagglutinin (HA) and/or neuraminidase (NA) polypeptides.

On account of their external localization the HA and NA antigens represent the most important viral target structures for the host immune system. Of antibodies which bind specifically to HA, it is thought that they neutralize the viral infectivity, probably by blocking the early steps of infection (Kida et al., 1983). NA-specific antibodies normally do not prevent the initial infection of a target cell but precisely the spread of the virus. In addition, due to competition mechanisms, the immunologic response to NA appears to be partly suppressed in favor of the more frequently occurring HA antigen (Kilbourne, 1976).

The neuraminidase (NA) assembles as a tetramer of four identical polypeptides and, when embedded in the envelope of the virus, accounts for approximately 10-20% of the total glycoproteins on the virion surface, with about 40-50 NA spikes and 300-400 HA spikes on an average sized virion of 120 nm (McAuley J. L. et al., 2019, Varghese et al., 1983; Ward et al., 1983; Moules et al., 2010). The four monomers, each of approximately 470 amino acids, fold into four distinct structural domains: the cytoplasmic tail, the transmembrane region, the stalk, and the catalytic head. Suggesting that the NA cytoplasmic tail is involved in critical viral functions, the N-terminal domain sequence is nearly 100% conserved across all IAV subtypes and consists of the sequence MNPNQK (SEQ ID NO:49; Blok and Air, 1982). Reverse engineered viruses containing site-specific mutations in this domain exhibit altered virion morphology and reduced replicative yields (Mitnaul et al., 1996; Jin et al., 1997; Barman et al., 2004). IAV engineered to encode an NA lacking a cytoplasmic tail could still be rescued but with a markedly attenuated phenotype (Garcia-Sastre and Palese, 1995). The altered morphology and attenuated infectivity of viruses expressing NA lacking the cytoplasmic tail domain are thought to be due to a lack of interaction with the membrane-associated matrix M1 viral protein (McAuley J. L. et al., 2019, Enami and Enami, 1996), which ultimately alters the efficiency of budding from the infected host cell (Jin et al., 1997; Ali et al., 2000; Barman et al., 2001; Mintaev et al., 2014). Determinants in both the cytoplasmic tail domain and the transmembrane domain contribute to the transport of the glycoprotein to the apical plasma membrane. However, the role of the tail domain in packaging the surface NA into virions remains unclear. A complete loss of the tail domain (Garcia-Sastre and Palese, 1995) resulted in a 50% reduction in the amount of NA in infected cells. The absence of all tail amino acids except for the initiating methionine gave rise to virus that also showed markedly less incorporation of NA into virions, but in this case, NA was present at the plasma membrane at similar levels to wild-type virus (McAuley J. L. et al., 2019, Mitnaul et al., 1996).

The terms "hemagglutinin" and "HA" refer to any influenza virus hemagglutinin. In certain embodiments, the hemagglutinin is influenza hemagglutinin, such as an influenza A hemagglutinin, an influenza B hemagglutinin, or an influenza C hemagglutinin. A typical hemagglutinin comprises domains known to those of skill in the art including a signal peptide (optional), a stem domain (also referred to as a "stalk domain"), a globular head domain, a luminal domain (optional), a transmembrane domain (optional) and a cytoplasmic domain (optional). Functionally, the hemagglutinin glycoprotein is composed of an immunodominant globular head domain involved in virus attachment to the host cell and the membrane proximal stalk/stem domain mediating fusion of the viral and cell membrane in the host endosome. The terms "stalk" and "stem" can be used interchangeably herein. The stalk domain is more conserved among influenza A (group 1 and 2) and B viruses allowing antibodies that target this region to neutralize a wide spectrum of influenza virus subtypes and is identified to harbor neutralizing B-cell epitopes. The immunodominant HA head domains undergo constant antigenic drift or shift The HA stalk domain is composed of three helical bundles and is functionally required for the pH induced conformational changes involved in membrane fusion during viral entry and exit from the host cell. In contrast to the HA-head variability, the stalk domain displays a much higher level of conservation across influenza strains with some central residues being identical across all subtypes (Krystal M, et al., 1982). The stalk domain is evolving at a rate that is significantly slower than that of the head domain. Additionally, the cross-reactive epitopes in the stalk domain targeted by broadly neutralizing monoclonal antibodies are evolving at an even slower rate compared to the full head and stalk regions of the protein (Kirkpatrick E. et al., 2018). Three protective epitopes, with varying levels of cross-reactivity between group 1 and 2 influenza strains, have been identified within the stalk portion of influenza A HA. Epitope 1 is centered on the α-helix of the HA2 region of HA. Targeting this epitope is also protective against B strains, but the antibody must have unique properties to accommodate key modifications helping to obscure the epitope surface (Dreyfus C, et al, 2012). Epitopes 2 and 3 are protective across group 2 influenza A subtypes. Epitope 2 includes the upper portion of the long alpha helix CD in HA2 (Wang T T, et al., 2010) whereas epitope 3 is located at the base of the HA2 stalk spanning regions of the fusion peptide and helix-capping loops (Ekiert D C, et al., 2011). The fourth protective stalk epitope is located in the C terminal portion of HA1 and offers broad protection across both B strain lineages (Yasugi M, et al., 2013) Generating a strong antibody response against any of these conserved epitopes can offer broader and more durable protection against influenza by circumventing reliance on epitopes prone to antigenic drift.

Specifically, the influenza virus is a high growth influenza virus specifically comprising one or more amino acid substitutions in the PB1, M and NS2 proteins as described in WO2020152318A. Specifically, the influenza virus described herein comprises a D67N amino acid substitution in the PB1 protein (according to the numbering of SEQ ID NO:22), a K93R substitution in the M protein (according to the numbering of SEQ ID NO:23) and a Y117H substitution in NS2/NEP protein (according to the numbering of SEQ ID NO:24).

Specifically, the influenza virus expressing the fusion protein described herein comprises any one or more of SEQ ID NOs 22, 23 or 24. More specifically, the influenza virus comprises all of SEQ ID NOs 22 to 24.

As an example, but not limited to it, influenza/SARS-CoV-2 chimeric viruses can be created by reverse genetics whereby the HA and NA genes can be derived from strains such as B/Florida/04/2006 (B-Yamagata lineage) and B/Murmansk/3/2010 (B Victoria lineage) while the internal genes are derived from B/Thüringen/02/2006 a B/Jiangsu/10/2003-like virus from the B Yamagata lineage. The NS gene is genetically modified to have a complete deletion of the NS1 gene. The NS1 deletion is replaced by 219 amino acids from the SARS-CoV-2 receptor binding domain (RBD) sequence which is flanked by sequences allowing efficient expression and secretion from infected cells. 6:2 reassortant viruses can be created using both unmodified internal genes: PB2. PB1, PA, NP, M and NS2/NEP as well as amino acid substitutions described above.

The term "transmembrane domain" (TMD) refers to any polypeptide which is hydrophobic and can be inserted or is anchored in the cellular membrane. Transmembrane domains (TMDs) consist predominantly of nonpolar amino add residues and may traverse the bilayer once or several times. Examples for TMDs can be, but are not limited to viral TMDs, Influenza TMD, tyrosine kinase TMD, G-protein-coupled receptors, EGF like domains SAE like domains or the transmembrane domain M2.

The term "antigenically different" as used herein refers to the presence of different antigenic sites being target by antibody response. Different antigenicity can be due to amino acid substitutions in the HA head domains due to antigenic drifts and shifts of the influenza virus. The 'classical' antigenic sites were historically determined using murine mAbs and analysis of changes in amino acid sequences connected to antigenic drift (as measured by reduction of HI activity (Wiley et al., N1981). The majority of mutations in the head were focused on sites related to immune escape, while the majority of mutations in the stalk seem to be evenly dispersed throughout the domain. (Kirkpatrick et al., 2018).

As used herein, the term "infection" means the invasion by, multiplication and/or presence of a virus in a cell or a subject. An infection can be an "active" infection, i.e., an infection in which the virus is replicating in a cell or a subject. Such an infection is characterized by the spread of the virus to other cells, tissues, and/or organs, from the cells, tissues, and/or organs initially infected by the virus. An infection may also be a latent infection, i.e. an infection in which the virus is not replicating. In certain embodiments, an infection refers to the pathological state resulting from the presence of the virus in a cell or a subject, or by the invasion of a cell or subject by the virus. Herein, infection is infection with coronavirus, or infection with both, coronavirus and influenza virus.

As used herein, the term "influenza virus disease" refers to the pathological state resulting from the presence of an influenza (e.g., influenza A or B) virus in a cell or subject or the invasion of a cell or subject by an influenza virus. In specific embodiments, the term refers to a respiratory illness caused by an influenza virus.

As used herein, the term "corona virus disease" refers to the pathological state resulting from the presence of a coronavirus (e.g., β-coronavirus, such as but not limited to SARS-CoV-2, MERS-CoV, SARS-CoV-1, HCoV-OC43, and HCoV-HKU1) virus in a cell or subject or the invasion of a cell or subject by a coronavirus. In specific embodiments, the term refers to a respiratory illness caused by a coronavirus.

As used herein, the term "nucleic acid" includes DNA molecules (e.g., cDNA) and RNA molecules (e.g., mRNA or pre-mRNA) and analogs of the DNA or RNA generated using nucleotide analogs. The nucleic acid can be single-stranded or double-stranded.

As used herein, the terms "prevent", "preventing" and "prevention" in the context of the administration of a therapy to a subject to prevent a coronavirus infection and/or an influenza virus infection refer to one or more of the prophylactic/beneficial effects resulting from the administration of a therapy or a combination of therapies. In a specific embodiment, the term "prevent" in the context of the administration of a therapy to a subject to prevent a coronavirus disease and optionally also an influenza virus disease refer to one or more of the following effects resulting from the administration of a therapy or a combination of therapies: (i) the inhibition of the development or onset of a coronavirus/an influenza virus disease or a symptom thereof; (ii) the inhibition of the recurrence of a coronavirus/an influenza virus disease or a symptom associated therewith; and (iii) the reduction or inhibition in coronavirus/influenza virus infection and/or replication.

Specifically, the term "prophylaxis" or "prophylactic" refers to preventive measures which are intended to reduce the risk of disease occurrence, or recurrence of disease. When provided prophylactically, the pharmaceutical preparation described herein which is a vaccine is provided before any symptom or clinical sign of a pathogen infection becomes manifest. The prophylactic administration of the preparation serves to prevent or attenuate any subsequent infection. When provided prophylactically, the preparation of the invention is provided before any symptom or clinical sign of a disease becomes manifest. The prophylactic administration of the preparation serves to prevent or attenuate one or more symptoms or clinical signs associated with the disease.

As used herein, the terms "treat," "treatment," and "treating" refer to prophylactic treatment, i.e. to the immunization or vaccination of a subject.

The "protection" provided need not be absolute, i.e., a corona infection need not be totally prevented or eradicated, as long as there is a statistically significant improvement compared with a control population or set of mammals, specifically of humans. Protection may be limited to reducing the severity or rapidity of onset of symptoms or clinical signs of the coronavirus infection.

As used herein, the terms "subject" or "patient" are used interchangeably to refer to an animal (e.g., birds, reptiles, and mammals). In a specific embodiment, the subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, the subject is a non-human animal. In some embodiments, the subject is a farm animal or pet. In another embodiment, the subject is a human.

According to a specific embodiment, the vaccine comprising the inventive recombinant influenza virus encoding the NS1-SARS-CoV-2-RBD fusion protein, or the two-component vaccine containing said virus can further comprise one or more adjuvants. As used herein, an "adjuvant" refers to a substance or mixture that enhances the body's immune response to an antigen, in the present disclosure an adjuvant enhances the cell mediated immune response induced by the combination of the first composition, second composition and/or third composition. As used herein, an adjuvant is combined into any or all of the priming composition and/or boosting composition.

The term "stabilizers" refers to any agent that can increase the stability of the virus, for example it can be bovine serum albumin, sugars, chitosan, dextrans, PEGs etc.

By "administration" is meant introducing the pharmaceutical preparation (vaccine) or two-component vaccine (herein referred to as preparation) of the present disclosure into a subject; it may also refer to the act of providing the preparation/vaccine of the present disclosure to a subject (e.g., by prescribing). The preparation can be administered to a human or animal subject in vivo using a variety of known routes and techniques. For example, the preparation may be provided as an injectable solution, suspension or emulsion and administered via parenteral, subcutaneous, oral, epidermal, intradermal, intramuscular, intraarterial, intraperitoneal, intravenous injection using a conventional needle and syringe, or using a liquid jet injection system. The preparation may be administered topically to skin or mucosal tissue, such as nasally, intratracheally, intestinally, sublingually, rectally or vaginally, or provided as a finely divided spray, such as a mist, suitable for respiratory or pulmonary administration. In certain embodiments, the preparations are administered intramuscularly or intranasally.

The term "effective amount" refers to that amount of the compound being administered which will produce a reaction that is distinct from a reaction that would occur in the absence of the compound. In reference to embodiments of the disclosure including the immunotherapy compounds of the disclosure, an "effective amount" is the amount which increases the immunological response in the recipient over the response that would be expected without administration of the compound.

The terms "pharmaceutical preparation" or "pharmaceutical composition" or "pharmaceutical formulation" refer to the recombinant influenza virus comprising a modified NS1 segment and encoding the NS1-SARS-CoV-2-RBD fusion protein as described herein, with other chemical components, such as pharmaceutically acceptable carriers and excipients. One purpose of a pharmaceutical composition is to facilitate administration of a compound to the organism.

As used herein, a "pharmaceutically acceptable carrier" refers to a carrier or diluent that does not cause significant irritation to an organism and does not abrogate the biological activity and properties of the administered vaccine compositions. It refers to a diluent, adjuvant, excipient, or vehicle with which the pharmaceutical composition (e.g., immunogenic or vaccine formulation) is administered. Saline solutions and aqueous dextrose and glycerol solutions can also be employed as liquid carriers, particularly for injectable solutions. Suitable excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should be selected according to the mode of administration. The particular formulation may also depend on whether the virus is live or inactivated.

The general concept of a prime-boost regimen is well known to the skilled person in the vaccine field. Thus, in one embodiment, the recombinant influenza virus comprising a modified NS1 segment, encoding the NS1-SARS-CoV-2-RBD fusion protein described herein can be part of a priming composition of a two-component vaccine composition used for priming an immune response, the boosting composition is a booster vaccine used for boosting an immune response. Because the prime boost effect is due to different antigenicity, the recombinant influenza virus comprising a modified NS1 segment, encoding the NS1-SARS-CoV-2-RBD fusion protein can also be part of the boosting vaccine composition.

As described herein, the first, priming composition is administered as a prime dose and the second boosting composition is administered as a boost dose, provided both the first and second compositions are administered. In embodiments, the prime and boost dose are administered 2 to 4 weeks, specifically at least 7 days, at least 14 days, at least 21 days, specifically at least 28 days apart, or longer. In embodiments, the prime dose and boost dose are administered about 7 days, about 14 days, about 21 days apart, about 28 days apart, about 35 days apart, about 42 days apart, about 49 days apart, 56 days, 63 days, 70 days, 77 days, 84 days, 91 days, 98 days, 105 days, 112, 119 days, 126 days, 133 days, 140 days, 147 days, 154 days, 161 days, 168 days, about 175 days, or about 183 days apart.

In certain embodiments, the prime administration and boost administration are administered about 1 week apart, about 2 weeks apart, about 3 weeks apart, about 4 weeks apart, about 5 weeks apart, about 6 weeks apart, about 7 weeks apart, about 8 weeks apart, about 9 weeks apart, about 10 weeks apart, about 11 weeks apart, about 12 weeks apart, about 13 weeks apart, about 14 weeks apart, about 15 weeks apart, about 16 weeks apart, about 17 weeks apart, about 18 weeks apart, about 19 weeks apart, about 20 weeks apart, about 21 weeks apart, about 22 weeks apart, about 23 weeks apart, about 24 weeks apart, about 25 weeks apart, about 26 weeks apart, about 27 weeks apart, about 28 weeks apart, about 29 weeks apart, or about 30 weeks apart In certain other embodiments, the prime dose and boost dose are administered about 1 month apart, about 2 months apart, about 3 months apart, about 4 months apart, about months apart, about 6 months apart, about 7 months apart, about 8 months apart, about 9 months apart, about 10 months apart, about 11 months apart, or about 12 months apart.

As general guidance, an immunologically effective amount when used with reference to a viral vaccine can range from about $1\times10^7$ viral particles per dose to about $1\times10^{12}$ viral particles per dose. An immunologically effective amount can be about $6\times10^{10}$, about $7\times10^{10}$, about $8\times10^{10}$, about $9\times10^{10}$, about $1\times10^{11}$, viral particles per dose.

The kit for prime-boost vaccination as referred herein comprises at least two separate vials:

the first vial contains a priming composition consisting of Victoria or Yamagata influenza B virus backbone and comprising the recombinant influenza virus comprising a modified NS1 segment, encoding the NS1-SARS-CoV-2-RBD fusion protein, specifically containing an effective amount in the range of about $7\times10^{10}$ to $8\times10^{10}$ TCID50, and the second vial contains a boosting composition also comprising an influenza virus of the same group comprising the recombinant influenza virus comprising a modified NS1 segment, encoding the NS1-SARS-CoV-2-RBD fusion protein as in the priming composition but differing in the HA head, specifically containing an effective amount of about $7\times10^{10}$ to $8\times10^{10}$ TCID50, and optionally a leaflet comprising information on the appropriate administration sequence and dosage.

The influenza virus as described herein can be also useful to prepare reassortant viruses including 6:1:1 reassortants, 6:2 reassortants and 7:1 reassortants. A 6:1:1 reassortant according to the present invention is an influenza virus with 6 internal gene segments, an NA gene segment from a different, second, viral isolate, and a HA gene segment from a third isolate; a 6:2 reassortant is an influenza virus with 6 internal gene segments, and an NA gene segment and a HA gene segment from a different (second) viral isolate; and a 7:1 reassortant is an influenza virus with 6 internal gene segments and an NA gene segment from a vaccine virus, and a HA gene segment from a different viral source than the vaccine virus, or an influenza virus with 6 internal gene segments and a HA gene segment, and an NA gene segment is from a different viral source than the vaccine virus. As an alternative, 5:1:2 reassortants are also encompassed herein.

In some embodiments, a plurality of vectors incorporating at least the 6 internal genome segments of a one influenza B strain along with one or more genome segments encoding immunogenic influenza surface antigens of a different influenza strain are introduced into a population of host cells. For example, at least the 6 internal genome segments ("the backbone") of a selected influenza A or B strain, e.g., an artificially engineered influenza A or B backbone strain encoding the recombinant influenza virus comprising a modified NS1 segment, encoding the NS1-SARS-CoV-2-RBD fusion protein as described herein, e.g. but not limited to B/Thüringen/02/06, B/Colorado, B/Iowa, B/Maryland, B/Phuket/3073/2013, a B/Jiangsu/10/03-like virus from the B Yamagata lineage, B/Murmansk/3/2010, or A/IVR-116 are introduced into a population of host cells along with one or more segments encoding immunogenic antigens derived from another virus strain. Typically, the immunogenic surface antigens include either or both of the hemagglutinin (HA) and/or neuraminidase (NA) antigens. In embodiments where a single segment encoding an immunogenic surface antigen is introduced, the 7 complementary segments of the selected virus are also introduced into the host cells.

In a further embodiment, herein provided is a plurality of influenza virus vectors for preparing a reassortant influenza B virus comprising a modified NS1 segment, encoding the NS1-SARS-CoV-2-RBD fusion protein described herein, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA encoding a fusion protein comprising from its N to C-terminus a truncated NS1 protein consisting of 10 to 20 amino acids of the N-terminus of the respective wild type NS1 protein, optionally a linker sequence, optionally a 2A self-cleaving peptide, specifically a P2A sequence, a signal peptide, a SARS-CoV receptor binding domain, optionally comprising about 10 to 50 additional amino acids of the SARS-CoV S1 subunit at its C-terminus, and linked to a transcription termination sequence, optionally fused to a transmembrane domain sequence, and optionally b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

In a further embodiment, herein provided is a plurality of influenza virus vectors, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA encoding a modified NS segment, encoding a fusion protein comprising from its N to C-terminus a truncated NS1 protein consisting of 10 to 20 amino acids of the N-terminus of the respective wild type NS1 protein, optionally a linker sequence, optionally a 2A self-cleaving peptide, specifically a P2A sequence, a signal peptide, a SARS-CoV receptor binding domain, specifically SARS-CoV-2 RBD, optionally comprising about 10 to 50 additional amino acids of the SARS-CoV S1 subunit at its C-terminus, optionally fused to a transmembrane domain sequence and b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

In a further embodiment, herein provided is a plurality of influenza virus vectors, comprising a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA encoding a modified NS segment, encoding a fusion protein comprising from its N to C-terminus truncated NS1 protein consisting of 10 to 20 amino acids of the N-terminus of the respective wild type NS1 protein, optionally a linker sequence, optionally a 2A self-cleaving peptide, specifically a P2A sequence, a signal peptide, a SARS-CoV receptor binding domain, optionally comprising about 10 to 50 additional amino acids of the SARS-CoV S1 subunit at its C-terminus, optionally fused to a transmembrane sequence and linked to a transcription termination sequence, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

According to yet a further embodiment of the invention, herein provided is a method for preparing an influenza virus B described herein, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA encoding a modified NS segment, encoding a fusion protein comprising from its N to C-terminus a truncated NS1 protein consisting of 10 to 20 amino acids of the N-terminus of the respective wild type NS1 protein, optionally a linker sequence, optionally a 2A self-cleaving peptide, specifically a P2A sequence, a signal peptide, a SARS-CoV receptor binding domain, specifically SARS-CoV-2 RBD, optionally comprising about 10 to 50 additional amino acids of the SARS-CoV S1 subunit at its C-terminus, optionally fused to a transmembrane sequence and linked to a transcription termination sequence, and optionally b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

Further provided in an embodiment is a method for preparing an influenza virus B of the present invention, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA encoding a modified NS segment, encoding a fusion protein comprising from its N to C-terminus a truncated NS1 protein consisting of 10 to 20 amino acids of the N-terminus of the respective wild type NS1 protein, optionally a linker sequence, optionally a 2A self-cleaving peptide, specifically a P2A sequence, a signal peptide, a SARS-CoV receptor binding domain, specifically SARS-CoV-2 RBD, optionally comprising about 10 to 50 additional amino acids of the SARS-CoV S1 subunit at its C-terminus, optionally fused to a transmembrane sequence and linked to a transcription termination sequence, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

In a further aspect, provided herein is a method for preparing an influenza virus A described herein, by contacting a cell with a) a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA encoding a recombinant influenza virus comprising a modified NS segment, encoding a fusion protein comprising from its N to C-terminus a truncated NS1 protein consisting of 10 to 20 amino acids of the N-terminus of the respective wild type NS1 protein, optionally a linker sequence, optionally a 2A self-cleaving peptide, specifically a P2A sequence, a signal peptide, a SARS-CoV receptor binding domain, specifically SARS-CoV-2 RBD, optionally comprising about 10 to 50 additional amino acids of the SARS-CoV S1 subunit at its C-terminus, optionally fused to a transmembrane sequence and linked to a transcription termination sequence, b) a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

EXAMPLES

The examples described herein are illustrative of the present invention and are not intended to be limitations thereon. Different embodiments of the present invention have been described according to the present invention. Many modifications and variations may be made to the techniques described and illustrated herein without departing from the scope of the invention. Accordingly, it should be understood that the examples are illustrative only and are not limiting upon the scope of the invention.

Example 1

A) Soluble Expression of Sars-CoV-2 RBD by Influenza delNS1 Virus.

Several variants of the Delta-19 SARS-CoV-2 strains with Influenza B (Delta-19: deltaNS, Covid 19; Table 1) were constructed. All strains express a secreted, soluble form of the SARS-CoV-2 Receptor Binding Domain (RBD) All strains were passaged at least 7 times and SARS-COV-2 RBD stability was confirmed. SARS-CoV-2 expression has been measured by sandwich ELISA and western blot for some of the vaccine strains. The three highlighted strains were used in the pre-clinical animal study.

The influenza/SARS-CoV-2 chimeric viruses were created by reverse genetics: The HA and NA genes were derived from B/Florida/04/2006 (B-Yamagata lineage) and B/Murmansk/3/2010 (B Victoria lineage) while the internal genes were derived from B/Thüringen/02/2006 a B/Jiangsu/10/2003-like virus from the B Yamagata lineage. The NS gene is genetically modified to have a complete deletion of the NS1 gene. The NS1 deletion is replaced by 219 amino acids from the SARS-CoV-2 receptor binding domain (RBD) sequence which was flanked by sequences allowing efficient expression and secretion from infected cells. A schematic drawing is depicted in FIG. 1*a*. 6:2 reassortant viruses were created using both unmodified internal genes: PB2, PB1, PA, NP, M and NS2/NEP as well as with high growth internal genes mutations as indicated in WO2020152318A2. This includes D67N amino acid substitution in the PB1 protein, K93R substitution in the M protein and Y117H substitution in NS2/NEP.

B) Anchored expression of Sars-CoV-2 RBD by influenza delNS1 virus. To anchor the RBD sequence into the viral envelope, the RBD sequence is fused to a transmembrane sequence. A schematic drawing of the construct is shown in FIG. 1*b*. The resulting constructs show neutralizing antibodies and protection against challenge with Sars-CoV-2.

TABLE 1

Influenza B Delta-19 strains constructed.

| Name | Influenza | RBD | Variant | High Growth internal |
|---|---|---|---|---|
| D19-5 | B/Florida/04/06-like | 219 | none | |
| D19-6 | B/Florida/04/06-like | 219 | none | |
| D19-7 | B/Florida/04/06-like | 219 | none | |
| D19-28 | B/Murmansk/3/10 | 219 | none | |
| D19-29 | B/Murmansk/3/10 | 219 | none | |
| D19-42 | B/Phuket/3073/13 | 219 | none | HG YAM |
| D19-41 | B/Phuket/3073/13 | 219 | none | HG YAM |
| D19-11a | B/Florida/04/06-like | 219 | none | HG YAM |
| D19-12a | B/Florida/04/06-like | 219 | none | HG YAM |
| D19-30 | B/Murmansk/3/10 | 219 | none | HG YAM |
| D19-38 | B/Phuket/3073/13 | 219 | none | M K105L |
| D19-50 | B/Murmansk/3/10 | 219 | England: N501Y | |
| D19-51 | B/Phuket/3073/13 | 219 | England: N501Y | |
| D19-53 | B/Florida/04/06-like | 219 | England: N501Y | |
| D19-54 | B/Murmansk/3/10 | 219 | England: N501Y | |
| D19-55 | B/Phuket/3073/13 | 219 | England: N501Y | |
| D19-56 | B/Florida/04/06-like | 219 | South Africa: K417N, E484K & N501Y | |
| D19-57 | B/Murmansk/3/10 | 219 | South Africa: K417N, E484K & N501Y | |
| D19-58 | B/Phuket/3073/13 | 219 | South Africa: K417N, E484K & N501Y | |
| D19-60 | B/Florida/04/06-like | 223 | none | |
| D19-61 | B/Murmansk/3/10 | 223 | none | |
| D19-62 | B/Phuket/3073/13 | 223 | none | |
| D19-63 | B/Florida/04/06-like | 223 | Delta: T478K & L452R | HG YAM |
| D19-67 | B/Murmansk/3/10 | 223 | Delta: T478K & L452R | HG YAM |
| D19-65 | B/Phuket/3073/13 | 223 | Delta: T478K & L452R | HG YAM |
| D19-76 | B/Florida/04/06-like | 223 | none | HG YAM |
| D19-77 | B/Murmansk/3/10 | 223 | none | HG YAM |
| D19-78 | B/Phuket/3073/13 | 223 | none | HG YAM |
| D19-79 | B/Florida/04/06-like | 223 | Delta: T478K & L452R | HG YAM |
| D19-80 | B/Murmansk/3/10 | 223 | Delta: T478K & L452R | HG YAM |
| D19-81 | B/Phuket/3073/13 | 223 | Delta: T478K & L452R | HG YAM |

FIG. 1. Shows the in silico design of the influenza B delNS-RBD219 segment. RBD 219 and RBD 223 refer to regions of the SARS-CoV-2 receptor binding domain.

A cDNA coding for the RBD of SARS-CoV-2 virus was inserted into a modified NS segment of influenza B/Thueringen/2/06 that does not code for a functional NS1 protein. The NS1 protein was C-terminally truncated after amino acid 16. A cDNA coding for a fusion protein consisting of (from N-terminus to C-terminus) a linker (GSG), a 19 amino acid self-cleaving P2A sequence, a 20 amino acid signal peptide, and 219 amino acids from the SARS-CoV-2 receptor binding domain (RBD) was fused in frame to the C-terminus of the 16 amino acid NS1 protein resulting in the following protein:

(SEQ ID NO: 25)

MADNMTTTQIEVGPGAGSGATNFSLLKQAGDVEENPGPMKTDTLLLWVL

LLWVPRSHG*NITNLCPFGEVENATRFASVYAWNRKRISNCVADYSVLYN*

*SASFSTFKCYGVSPTKLNDLCFTNVYADSFVIRGDEVRQIAPGQTGKIA*

-continued

*DYNYKLPDDFTGCVIAWNSNNLDSKVGGNYNYLYRLFRKSNLKPFERDI*

*STEIYQAGSTPCNGVEGFNCYFPLQSYGFQPTNGVGYQPYRVVVLSFEL*

*LHAPATVCGPKKSTNLVKNKCVNFNFNGLTGT*.

(SEQ ID NO: 26)

MADNMTTTQIEVGPGA is the C-terminally truncated NS1 GSG is the linker (SEQ ID NO: 8)

ATNFSLLKQAGDVEENPGP is theP2A sequence (SEQ ID NO: 27)

MKTDTLLLWVLLLWVPRSHG is the signal peptide

-continued (SEQ ID NO: 28)

*NITNLCPFGEVENATRFASVYAWNRKRISNCVADYSVLYNSASFSTFKC*

*YGVSPTKLNDLCFTNVYADSFVIRGDEVRQIAPGQTGKIADYNYKLPDD*

*FTGCVIAWNSNNLDSKVGGNYNYLYRLFRKSNLKPFERDISTEIYQAGS*

*TPCNGVEGFNCYFPLQSYGFQPTNGVGYQPYRVVVLSFELLHAPATVCG*

*PKKSTNLVKNKCVNFNFNGLTGT* is the SARS-CoV-2 RBD sequence

SARS-CoV-2 Receptor Binding Domain may have the following sequence:

RBD219 (nt 22553-23209 in SARS-CoV-2 reference strain hCoV-19/Wuhan/Hu-1/2019 EPI ISL 402125, S Protein is nt 21536-25384)

(SEQ ID NO: 29)

AATATTACAAACTTGTGCCCTTTTGGTGAAGTTTTTAACGCCACCAGATTTGCATCT

GTTTATGCTTGGAACAGGAAGAGAATCAGCAACTGTGTTGCTGATTATTCTGTCCT

ATATAATTCCGCATCATTTTCCACTTTTAAGTGTTATGGAGTGTCTCCTACTAAATT

AAATGATCTCTGCTTTACTAATGTCTATGCAGATTCATTTGTAATTAGAGGTGATGA

AGTCAGACAAATCGCTCCAGGGCAAACTGGAAAGATTGCTGATTATAATTATAAAT

TACCAGATGATTTTACAGGCTGCGTTATAGCTTGGAATTCTAACAATCTTGATTCTA

AGGTTGGTGGTAATTATAATTACCTGTATAGATTGTTTAGGAAGTCTAATCTCAAAC

CTTTTGAGAGAGATATTTCAACTGAAATCTATCAGGCCGGTAGCACACCTTGTAAT

GGTGTTGAAGGTTTTAATTGTTACTTTCCTTTACAATCATATGGTTTCCAACCCACT

AATGGTGTTGGTTACCAACCATACAGAGTAGTAGTACTTTCTTTTGAACTTCTACAT

GCACCAGCAACTGTTTGTGGACCTAAAAAGTCTACTAATTTGGTTAAAAACAAATG

TGTCAATTTCAACTTCAATGGTTTAACAGGCACA

Amino Acid Sequence is AA 331-524 in the S Protein of the reference strain (SEQ ID NO: 30)

NITNLCPFGEVFNATRFASVYAWNRKRISNCVADYSVLYNSASFSTFKCYGVSPTKLN

DLCFTNVYADSFVIRGDEVRQIAPGQTGKIADYNYKLPDDFTGCVIAWNSNNLDSKVG

GNYNYLYRLFRKSNLKPFERDISTEIYQAGSTPCNGVEGENCYFPLQSYGFQPTNGV

GYQPYRVVVLSFELLHAPATVCGPKKSTNLVKNKCVNFNFNGLTGT

RBD223 (nt 22517-23185 in SARS-CoV-2 reference strain hCoV-19/Wuhan/Hu-1/2019 EPI ISL 402125, S Protein is nt 21536-25384)

(SEQ ID NO: 31)

AGAGTCCAgCCgACcGAATCTATTGTTAGATTTCCTAATATCACGAATCTGTGCCCC

TTTGGAGAGGTGTTCAATGCTACCCGCTTTGCTTCAGTGTACGCTTGGAATAGGA

AACGGATCAGTAATTGCGTGGCTGATTATTCTGTGCTGTACAATAGCGCAAGCTT

CAGCACATTCAAATGCTATGGAGTGAGCCCCACAAAACTGAATGATCTGTGCTTC

ACTAATGTTTACGCCGATTCATTTGTGATACGCGGAGATGAGGTGAGACAGATTG

CCCCTGGCCAAACAGGAAAAATCGCGGATTACAATTACAAACTGCCAGATGATTT

CACTGGATGCGTGATTGCATGGAATTCAAATAATCTGGATAGTAAAGTTGGAGGC

AATTACAATTACCTGTACAGACTGTTCAGAAAAAGCAATCTGAAACCCTTTGAGCG

AGATATCAGCACCGAAATCTACCAGGCTGGCTCTACGCCTTGCAATGGAGTGGAG

GGATTCAATTGTTATTTTCCTCTGCAGAGTTACGGATTCCAACCGACCAATGGTGT

GGGATATCAGCCCTACAGAGTGGTGGTGCTGAGCTTCGAACTGCTTCACGCTCC

-continued

AGCAACAGTGTGCGGACCCAAAAAATCTACTAATCTGGTGAAAAATAAGTGCGTG

AATTTC

Amino Acid Sequence is AA 319-514 in the S protein of the reference strain (SEQ ID NO: 32)

RVQPTESIVRFPNITNLCPFGEVFNATRFASVYAWNRKRISNCVADYSVLYNSASFST

FKCYGVSPTKLNDLCFTNVYADSFVIRGDEVRQIAPGQTGKIADYNYKLPDDFTGCVI

AWNSNNLDSKVGGNYNYLYRLFRKSNLKPFERDISTEIYQAGSTPCNGVEGFNCYFP

LQSYGFQPTNGVGYQPYRVVVLSFELLHAPATVCGPKKSTNLVKNKCVNF

Transmembrane Domain Sequence Information:

Flu B (B/Phuket/3073/2013) HA2 Transmembrane domain and Cytoplasmic Tail

Amino Acid Sequence:

Transmembrane Domain:

(SEQ ID NO: 33)

LLYYSTAASSLAVTLMLAIFIVYMV(S)

Cytoplasmic Tail:

(SEQ ID NO: 34)

RDNVSCSICL

Nucleotide Sequence:

Transmembrane Domain:

(SEQ ID NO: 35)

CTGCTCTATTACTCAACTGCTGCTTCTAGTTTGGCTGTAACATTAATGC
TAGCTATTTTTATTGTTTATATGGTCTCC

Cytoplasmic Tail:

(SEQ ID NO: 36)

AGAGACAACGTTTCATGCTCCATCTGTCTA

Flu A (A/Texas/04/2009) HA2 Transmembrane domain and Cytoplasmic Tail

Amino Acid Sequence:

Transmembrane Domain:

(SEQ ID NO: 37)

QILAIYSTVASSLVLVVSLGAISFWM(C)

Cytoplasmic Tail:

(SEQ ID NO: 38)

SNGSLQCRICI

Nucleotide Sequence:

Transmembrane Domain:

(SEQ ID NO: 39)

AGATTTTGGCGATCTATTCAACTGTCGCCAGTTCATTGGTACTGGTAGT
CTCCCTGGGGGCAATCAGTTTCTGGATGTGC

Cytoplasmic Tail:

(SEQ ID NO: 40)

TCTAATGGGTCTCTACAGTGTAGAATATGTATT

Transmembrane Construct Sequences:

Examples for transmembrane sequences which can be used according to the invention 1. BGHB deINS1-RBD219 BSMBI plus Flu B HA2 linker, transmembrane domain, and cytoplasmic tail from B/Phuket/3073/2013 (Codon optimized) nucleotide sequence (SEQ ID NO: 41)

AGGGAGCAGAAGCAGAGGATTTGTTTAGTCACTGGCAAACAGGAAAAAT

GGCGGACAATATGACCACAACACAAATTGAGGTGGGTCCGGGAGCAGGA

TCCGGAGCAACAAATTTCTCACTTCTTAAACAAGCAGGGGACGTGGAAG

AAAATCCAGGACCAATGAAAACAGATACACTTCTTCTTTGGGTGCTGCT

TTTGTGGGTTCCAAGATCACATGGGAATATCACGAATCTGTGCCCCTTT

GGAGAGGTGTTCAATGCTACCCGCTTTGCTTCAGTGTACGCTTGGAATA

GGAAACGGATCAGTAATTGCGTGGCTGATTATTCTGTGCTGTACAATAG

CGCAAGCTTCAGCACATTCAAATGCTATGGAGTGAGCCCCACAAAACTG

AATGATCTGTGCTTCACTAATGTTTACGCCGATTCATTTGTGATACGCG

GAGATGAGGTGAGACAGATTGCCCCTGGCCAAACAGGAAAAATCGCGGA

TTACAATTACAAACTGCCAGATGATTTCACTGGATGCGTGATTGCATGG

AATTCAAATAATCTGGATAGTAAAGTTGGAGGCAATTACAATTACCTGT

ACAGACTGTTCAGAAAAAGCAATCTGAAACCCTTTGAGCGAGATATCAG

CACCGAAATCTACCAGGCTGGCTCTACGCCTTGCAATGGAGTGGAGGGA

TTCAATTGTTATTTTCCTCTGCAGAGTTACGGATTCCAACCGACCAATG

GTGTGGGATATCAGCCCTACAGAGTGGTGGTGCTGAGCTTCGAACTGCT

TCACGCTCCAGCAACAGTGTGCGGACCCAAAAAATCTACTAATCTGGTG

AAAAATAAGTGCGTGAATTTCAATTTCAATGGACTGACGGGAACGGGA

*TTGGATAATCATACTATA*CTGCTTTACTACTCAACTGCTGCCTCCAGTT

TGGCTGTAACACTGATGATAGCTATCTTTGTTGTTTATATGGTCTCCAG

AGACAATGTTTCTTGCTCCATCTGTCTATAATGATGAGCGGCCGCCCAA

GCAGAAAGTGGTACTAACCTTCTTCTCTTTCTTCTCCTGACAGTGGAGG

ATGAAGAAGATGGCCATCGGATCCTCAATTCACTCTTCGAGCGTCTTAA

TGAAGGACATTCAAAGCCAATTCGAGCAGCTGAAACTGCGGTGGGAGTC

TTATCCCAATTTGGTCAAGAGCACCGATTATCACCAGAAGAGGGAGACA

ATTAGACTGGTCACGGAAGAACTTTATCTTTTAAGTAAAAGAATTGATG

ATAACATATTGTTCCACAAAACAGTAATAGCTAACAGCTCCATAATAGC

TGACATGGTTGTATCATTATCATTATTAGAAACATTGTATGAAATGAAG

GATGTGGTTGAAGTGTACAGCAGGCAGTGCTTGTGAATTTAAAATAAAA

ATCCTCTTGTTACTACTAATAC italic = Splice site bold = RBD219 bold, italic = Linker underlined = TM Domain

BGHB deINS1-RBD219 BSMBI plus Flu B HA2 linker, transmembrane domain, and cytoplasmic tail from B/Phuket/3073/2013 (Codon optimized) amino acid sequence NEP/NS2 (spliced)

(SEQ ID NO: 42)
MADNMTTTQIEWRMKKMAIGSSIHSSSVLMKDIQSQFEQLKLRWESYPN
LVKSTDYHQKRETIRLVTEELYLLSKRIDDNILFHKTVIANSSIIADMV
VSLSLLETLYEMKDVVEVYSRQCL

P2A Sequence (all in frame):

(SEQ ID NO: 8)
ATNFSLLKQAGDVEENPGP

Signal Peptide:

(SEQ ID NO: 27)
MKTDTLLLWVLLLWVPRSHG

SARS-CoV-2 RBD219

(SEQ ID NO: 43)
NITNLCPFGEVFNATRFASVYAWNRKRISNCVADYSVLYNSASFSTFKC
YGVSPTKLNDLCFTNVYADSFVIRGDEVRQIAPGQTGKIADYNYKLPDD
FTGCVIAWNSNNLDSKVGGNYNYLYRLFRKSNLKPFERDISTEIYQAGS
TPCNGVEGENCYFPLQSYGFQPTNGVGYQPYRVVVLSFELLHAPATVCG
PKKSTNLVKNKCVNFNFNGLTGT

Flu B HA2 Linker:

(SEQ ID NO: 44)
(G)LDNHTI

Transmembrane Domain:

(SEQ ID NO: 33)
LLYYSTAASSLAVTLMLAIFIVYMV(S)

Cytoplasmic Tail:

(SEQ ID NO: 34)
RDNVSCSICL

2. BGHB deINS1-RBD219 BSMBI plus generic linker, Flu B HA2 transmembrane domain, and cytoplasmic tail from B/Phuket/3073/2013 (Codon optimized) nucleotide sequence (SEQ ID NO: 45)
AGGGAGCAGAAGCAGAGGATTTGTTTAGTCACTGGCAAACAGGAAAAAT
GGCGGACAATATGACCACAACACAAATTGAGGTGGGTCCGGGAGCAGGA
TCCGGAGCAACAAATTTCTCACTTCTTAAACAAGCAGGGGACGTGGAAG
AAAATCCAGGACCAATGAAAACAGATACACTTCTTCTTTGGGTGCTGCT
TTTGTGGGTTCCAAGATCACATGGGAATATCACGAATCTGTGCCCCTTT
GGAGAGGTGTTCAATGCTACCCGCTTTGCTTCAGTGTACGCTTGGAATA
GGAAACGGATCAGTAATTGCGTGGCTGATTATTCTGTGCTGTACAATAG
CGCAAGCTTCAGCACATTCAAATGCTATGGAGTGAGCCCCACAAAACTG
AATGATCTGTGCTTCACTAATGTTTACGCCGATTCATTTGTGATACGCG
GAGATGAGGTGAGACAGATTGCCCCTGGCCAAACAGGAAAAATCGCGGA
TTACAATTACAAACTGCCAGATGATTTCACTGGATGCGTGATTGCATGG
AATTCAAATAATCTGGATAGTAAAGTTGGAGGCAATTACAATTACCTGT
ACAGACTGTTCAGAAAAAGCAATCTGAAACCCTTTGAGCGAGATATCAG
CACCGAAATCTACCAGGCTGGCTCTACGCCTTGCAATGGAGTGGAGGGA

-continued

TTCAATTGTTATTTTCCTCTGCAGAGTTACGGATTCCAACCGACCAATG
GTGTGGGATATCAGCCCTACAGAGTGGTGGTGCTGAGCTTCGAACTGCT
TCACGCTCCAGCAACAGTGTGCGGACCCAAAAAATCTACTAATCTGGTG
AAAAATAAGTGCGTGAATTTCAATTTCAATGGACTGACGGGAACGGGT
*AGT**GGTAGTGGTAGTGGTAGTGGT*CTGCTTTACTACTCAACTGCTGCCT
CCAGTTTGGCTGTAACACTGATGATAGCTATCTTTGTTGTTTATATGGT
CTCCAGAGACAATGTTTCTTGCTCCATCTGTCTATAATGATGAGCGGCC
GCCCAAGCAGAAAGTGGTACTAACCTTCTTCTCTTTCTTCTCCTGACAG
TGGAGGATGAAGAAGATGGCCATCGGATCCTCAATTCACTCTTCGAGCG
TCTTAATGAAGGACATTCAAAGCCAATTCGAGCAGCTGAAACTGCGGTG
GGAGTCTTATCCCAATTTGGTCAAGAGCACCGATTATCACCAGAAGAGG
GAGACAATTAGACTGGTCACGGAAGAACTTTATCTTTTAAGTAAAAGAA
TTGATGATAACATATTGTTCCACAAAACAGTAATAGCTAACAGCTCCAT
AATAGCTGACATGGTTGTATCATTATCATTATTAGAAACATTGTATGAA
ATGAAGGATGTGGTTGAAGTGTACAGCAGGCAGTGCTTGTGAATTTAAA
ATAAAAATCCTCTTGTTACTACTAATAC italic = Splice site
bold RBD219
bold, italic = Linker
underlined = TM Domain BGHB deINS1-RBD219 BSMBI plus generic linker, Flu B HA2 transmembrane domain, and cytoplasmic tail from B/Phuket/3073/2013 (Codon optimized) amino acid sequence NEP/NS2 (spliced)

(SEQ ID NO: 46)
MADNMTTTQIEWRMKKMAIGSSIHSSSVLMKDIQSQFEQLKLRWESYPN
LVKSTDYHQKRETIRLVTEELYLLSKRIDDNILFHKTVIANSSIIADMV
VSLSLLETLYEMKDVVEVYSRQCL

P2A Sequence (all in frame):

(SEQ ID NO: 8)
ATNFSLLKQAGDVEENPGP

Signal Peptide:

(SEQ ID NO: 27)
MKTDTLLLWVLLLWVPRSHG

SARS-CoV-2 RBD219

(SEQ ID NO: 47)
NITNLCPFGEVFNATRFASVYAWNRKRISNCVADYSVLYNSASFSTFKC
YGVSPTKLNDLCFTNVYADSFVIRGDEVRQIAPGQTGKIADYNYKLPDD
FTGCVIAWNSNNLDSKVGGNYNYLYRLFRKSNLKPFERDISTEIYQAGS
TPCNGVEGFNCYFPLQSYGFQPTNGVGYQPYRVVVLSFELLHAPATVCG
PKKSTNLVKNKCVNFNFNGLTGT

-continued

```
Generic Linker:
                                        (SEQ ID NO: 48)
(G)SGSGSGSG

Transmembrane Domain:
                                        (SEQ ID NO: 33)
LLYYSTAASSLAVTLMLAIFIVYMV(S)

Cytoplasmic Tail:
                                        (SEQ ID NO: 34)
RDNVSCSICL
```

Example 2

Serum free Vero cells were infected for 16 hours in infection media containing 500 ng/ml Amphotericin and 0.5% 10×TrypLE. Supernatant was collected, centrifuged at 200×g for 10 minutes and run on 4-20% SDS-PAGE gel with 2× Laemmli sample loading buffer with 2-Mercaptoethanol and boiling at 99° C. for 10 minutes. Proteins are transferred to nitrocellulose membrane using methanol free transfer buffer. Membranes are blocked with 5% milk and stained with either a mouse monoclonal antibody (SARS-COV-2 Spike RBD Mab Clone 1034522, RND Systems) and Goat anti Moue HRP secondary antibody or a Rabbit polyclonal antibody (SARS CoV-2/2019-nCoV Spike/RBD Antibody, Rabbit PAb, antigen affinity purified, Sino Biological) and Goat anti Rabbit IgG HRP (RND Systems). Membranes were washed with PBST and developed with Super Chemiluminescent substrate (Pierce). Protein bands were visualized using a Bio Rad Chem+ gel doc. Concentration of secreted RBD is estimated by comparing to a known control and using the Image Lab Quantitative Software from Bio Rad (FIG. 2).

Example 3

Analysis of RBD Expression by Immunofluorescent Staining in Relation to the Influenza Virus NP Protein Expression Serum free Vero cells were infected with a 1:5 serial dilution of undiluted virus in media containing 500 ng/ml Amphotericin. Infected cells were incubated at 33° C. overnight and fixed after 16-20 h with 4% formaldehyde. Cells were washed with PBS, permeabilized with 1% triton and washed with PBST. Two primary antibodies were added simultaneously: anti influenza B NP (clone B017, mouse, Invitrogen) and anti-SARS CoV-2 Neutralizing Antibody (4C6, mAB, rabbit, Genscript) in 5% mill in PBST, washed 3 times with PBST and incubated with 2 secondary antibodies: Goat anti Mouse IgG conjugated with Dylight 488 (Pierce) and Goat anti rabbit IgG AlexaFluor 647 (Jackson Immuno Research Laboratories). Cells were then washed 3 times with PBST and fluorescent cells were imaged using the Celigo Imaging Cytometer (Nexcelom). Each well was counted in both the green (NP) and red channel (RBD) and titers were calculated. The titers shown below in Table 2 represent the number of cells expressing NP and RBD upon infection with the indicated viral vectors each derived from passage 8. This result indicates that almost every cell infected with the virus (=NP titer) expresses the inserted RBD antigen. Importantly, the ratio of NP versus RBD expression remained in the same range during the passages, indicating that expression of the RBD is stable. Moreover, the results show that the titers are sufficiently high (>8 log 10) to permit vaccine production on an industrial scale. The RBD ratios of the seed viruses are shown below. The RBD ratios of the different passages are shown in FIG. 3.

TABLE 2

| Virus | NP titer (log10 FFU/ml) | RBD Titer (log10 FFU/ml) |
|---|---|---|
| B/Florida/04/2006 Delta-19 | 8.13 | 7.92 |
| B/Murmansk/3/2010 Delta-19 | 8.31 | 8.22 |

Example 4

Stability

Each vaccine virus was passaged 7 times (P1-7) in serum free Vero Cells in media containing 0.5% 10×TrypLE and 500 ng/ml Amphotericin B. Genetic stability was assessed by RT-PCR. Briefly, RNA was extracted from each passage and RT-PCR was performed using One step RT-PCR kit (Qiagen) using NS non-coding region primers. PCR products were run on a 0.8% agarose gel (FIG. 3). Identity was confirmed by sequencing.

Example 5

Growth Kinetics of Chimeric Vaccine Viruses

Growth of the viruses were assessed by infecting serum free Vero cells in T25 flasks with cells seeded at 80,000 cells/cm2 at an MOI of 0.005 in media containing 0.5% 10×TrypLE and 500 ng/ml Amphotericin B at a ratio of 0.22 ml/$cm^2$. At 48 hours post infection, the supernatants were spiked with 0.5% 10×TrypLE. Supernatant was harvested at 48, 72 and 96 hours post infection and supernatants were titered by FFA assay. The results are shown in FIG. 4.

FIG. 4 *a* shows the B/Florida Delta-19 P7 growth curve on serum free Vero cells seeded at 80,000 C/Cm2 were infected at an MOI of 0.005 in 0.22 ml virus growth media/cm2. Virus growth media contains 0.5% 10× TrypLE and 500 ng/ml AmphB. Samples were collected at 28, 72 and 96 hours post infection and titered by FFA assay.

FIG. 4 *b* shows B/Murmansk Delta-19 P4 Growth Curve on serum free Vero cells seeded at 80,000 C/Cm2 were infected at an MOI of 0.005 in 0.22 ml virus growth media/cm2. Virus growth media contains 0.5% 10×TrypLE and 500 ng/ml AmphB. Samples were collected at 28, 72 and 96 hours post infection and titered by multiplex FFA assay.

Example 6

Animal Study. Immunogenicity and Protection Efficacy of Delta-19 Against SARS-CoV-2 Wild-Type Challenge The immunogenic properties and protection efficacy of the Delta-19 vaccine in the ferret model was evaluated. Three Delta-19 strains with different Influenza B backbones were used in this study: B/Florida/04/06-like (B-Yamagata), B/Phuket/3073/2013 (B-Yamagata) and B/Murmansk/3/10 (B-Victoria) that all express a 219 amino acid region of the SARS-CoV-2 S1 protein, the Receptor Binding Domain (RBD) (Amino Acids:331-524 in the S protein of hCov-19/Wuhan/Hu-1/2019/reference strain). All strains used in the pre-clinical study contained the wild-type NS splice mutant. Each animal received prime and booster inoculations of these three strains at a dose of $10^{8.0}$-$10^{8.7}$). Sera was collected at various points throughout the study. The ferrets were challenged with 5e4 pfu/500 ul IN with SARS-CoV- 2/WA01, CSU V2 from BEI, 3/5/21 21 days post boost 3. Plaque Reduction Neutralizing Titers (PRNT) were measured against SARS-CoV-2 in sera (Table 3). Nasal wash and oral swab samples were collected at days 1, 3, 5 and 7 post challenge. SARS-CoV-2 levels were measured in these samples by traditional plaque assay (Tables 4 and 5). The sera was also used to measure the serum IgG levels against SARS-CoV-2 RBD (Table 6), Influenza HA0 (Table 7) and neutralizing titers against the three influenza strains (Table 8) were measured by Fluorescent Microneutralization Assay (fMNA). Weight, temperature, and clinical symptoms were measured in all ferrets throughout the study. Six out of eight ferrets immunized developed neutralizing antibodies and were protected against challenge with SARS COV-2. All immunized ferrets had also neutralizing antibodies against influenza virus indicating that dual protection against Covid19 and influenza is possible with the chimeric constructs that were generated and described.

TABLE 3

50% Plaque Reduction Neutralizing Titers (PRNT50) against wild-type SARS-CoV-2

| Animal | Pre-immunization | Pre-challenge |
|---|---|---|
| 1 | <10 | 10 |
| 2 | <10 | 10 |
| 3 | <10 | >320 |
| 4 | <10 | 40 |
| 5 | <10 | 160 |
| 6 | <10 | >320 |
| 7 | <10 | 40 |
| 8 | 10 | >320 |

TABLE 4

Viral load in the nasal wash, plaque assay (PFU/ml)

| Ferret | Day 1 (PFU/ml) | Day 3 (PFU/ml) | Day 5 (PFU/ml) | Day 7 (PFU/ml) |
|---|---|---|---|---|
| 1 | 40 | 1500 | 140 | <10 |
| 2 | 80 | 1900 | 110 | <10 |
| 3 | <10 | <10 | <10 | <10 |
| 4 | <10 | 40 | <10 | <10 |
| 5 | 20 | 60 | <10 | <10 |
| 6 | 20 | 40 | <10 | <10 |
| 7 | 20 | 30 | <10 | <10 |
| 8 | <10 | 20 | <10 | <10 |
| Control 1 | 80 | 2600 | 140 | <10 |
| Control 2 | 740 | 4600 | 640 | <10 |
| Control 3 | 130 | 5200 | 210 | <10 |
| Control 4 | 420 | 4100 | 220 | <10 |

TABLE 5

Viral load in the Oral Swab, Plaque Assay (PFU/ml)

| Ferret | Day 1 (PFU/ml) | Day 3 (PFU/ml) | Day 5 (PFU/ml) | Day 7 (PFU/ml) |
|---|---|---|---|---|
| 1 | 20 | 1700 | 30 | <10 |
| 2 | 40 | 850 | 110 | <10 |
| 3 | <10 | <10 | <10 | <10 |
| 4 | <10 | <10 | <10 | <10 |
| 5 | 20 | <10 | <10 | <10 |
| 6 | <10 | <10 | <10 | <10 |
| 7 | <10 | <10 | <10 | <10 |
| 8 | <10 | <10 | <10 | <10 |
| Control 1 | 120 | 1100 | 80 | <10 |
| Control 2 | 220 | 550 | 480 | <10 |
| Control 3 | 180 | 3200 | 60 | <10 |
| Control 4 | 220 | 2200 | 450 | <10 |

TABLE 6

Serum IgG SARS-CoV-2 Receptor Binding Domain (RBD)

| Ferret | Pre-Immune | Pre-Challenge |
|---|---|---|
| 1 | 32 | 3444 |
| 2 | 16 | 18 |
| 3 | 16 | 14 |
| 4 | 16 | 4096 |
| 5 | 16 | 2048 |
| 6 | 16 | 1448 |
| 7 | 32 | 2896 |
| 8 | 32 | 1448 |
| Control 1 | NA | 12 |
| Control 2 | NA | 8 |
| Control 3 | NA | 14 |
| Control 4 | NA | 10 |

TABLE 7

Serum IgG Influenza HA0

| | B/Brisbane/60/2006 (B-Vic) HA0 | | B/Phuket/3073/13 (B-Yam) HA0 | | B/Florida/04/06 (B-Yam) HA0 | |
|---|---|---|---|---|---|---|
| Ferret | Pre-Immune | Pre-Challenge | Pre-Immune | Pre-Challenge | Pre-Immune | Pre-Challenge |
| 1 | 16 | 4096 | 23 | 8192 | 23 | 8192 |
| 2 | 13 | 8192 | 16 | 8192 | 13 | 8192 |
| 3 | 9 | 2580 | 16 | 5793 | 13 | 2896 |
| 4 | 11 | 2580 | 16 | 2048 | 11 | 5793 |
| 5 | 13 | 6502 | 23 | 4096 | 11 | 4096 |
| 6 | 13 | 3251 | 16 | 4096 | 13 | 1448 |
| 7 | 13 | 4096 | 16 | 2048 | 16 | 724 |

TABLE 7-continued

| Serum IgG Influenza HA0 | | | | | | |
|---|---|---|---|---|---|---|
| | B/Brisbane/60/2006 (B-Vic) HA0 | | B/Phuket/3073/13 (B-Yam) HA0 | | B/Florida/04/06 (B-Yam) HA0 | |
| Ferret | Pre-Immune | Pre-Challenge | Pre-Immune | Pre-Challenge | Pre-Immune | Pre-Challenge |
| 8 | 20 | 5161 | 23 | 4096 | 16 | 1448 |
| Control 1 | NA | 13 | NA | 128 | NA | 161 |
| Control 2 | NA | 10 | NA | 81 | NA | 38 |
| Control 3 | NA | 10 | NA | 8 | NA | 11 |
| Control 4 | NA | 11 | NA | 23 | NA | 16 |

TABLE 8

| 90% fluorescent Micro Neutralizing Assay (fMNA90) against Influenza vaccine strains | | | | | | |
|---|---|---|---|---|---|---|
| | B/Murmansk/3/10 Delta-19 | | B/Phuket/3073/13 Delta-19 | | B/Florida/04/06 Delta-19 | |
| Ferret | Pre-Immune | Pre-Challenge | Pre-Immune | Pre-Challenge | Pre-Immune | Pre-Challenge |
| 1 | 8 | 128 | 8 | 512 | 8 | 256 |
| 2 | 8 | 4096 | 8 | 512 | 8 | 256 |
| 3 | 8 | 128 | 8 | 1024 | 8 | 256 |
| 4 | 8 | 128 | 8 | 4096 | 8 | 512 |
| 5 | 8 | 1024 | 8 | 256 | 8 | 256 |
| 6 | 8 | 1024 | 8 | 512 | 8 | 512 |
| 7 | 8 | 1024 | 8 | 64 | 8 | 64 |
| 8 | 8 | 512 | 8 | 256 | 8 | 512 |
| Control 1 | NA | 8 | NA | 8 | NA | 8 |
| Control 2 | NA | 8 | NA | 8 | NA | 8 |
| Control 3 | NA | 8 | NA | 8 | NA | 8 |
| Control 4 | NA | 8 | NA | 8 | NA | 8 |

REFERENCES

Ali et al., 2000, Influenza virus assembly: effect of influenza virus glycoproteins on the membrane association of M1 protein. *J. Virol.* 74, 8709-8719. doi: 10.1128/JVI.74.18.8709-8719.2000

Barman et al., 2001, Transport of viral proteins to the apical membranes and interaction of matrix protein with glycoproteins in the assembly of influenza viruses. *Virus Res.* 77, 61-69. doi: 10.1016/S0168-1702(01)00266-0

Barman et al., 2004, Role of transmembrane domain and cytoplasmic tail amino acid sequences of influenza a virus neuraminidase in raft association and virus budding. *J. Virol.* 78, 5258-5269. doi: 10.1128/JVI.78.10.5258-5269.2004

Blok and Air, 1982, Variation in the membrane-insertion and "stalk" sequences in eight subtypes of influenza type A virus neuraminidase. *Biochemistry* 21, 4001-4007

Dreyfus C, et al, 2012, Highly conserved protective epitopes on influenza B viruses, *Science.* 337:1343-1348

Enami and Enami, 1996, Influenza virus hemagglutinin and neuraminidase glycoproteins stimulate the membrane association of the matrix protein. *J. Virol.* 70, 6653-6657

Ekiert D C, et al., 2011, A highly conserved neutralizing epitope on group 2 influenza A viruses, *Science* 333: 843-850

Garcia-Sastre and Palese, 1995, The cytoplasmic tail of the neuraminidase protein of influenza A virus does not play an important role in the packaging of this protein into viral envelopes. *Virus Res.* 37, 37-47. doi: 10.1016/0168-1702(95)00017-K Ferko B. et al., 2004, Immunogenicity and protection efficacy of replication-deficient influenza A viruses with altered NS1 genes, *J. Virol.,* 78(23), 13037-45

Jin et al., 1997; Influenza virus hemagglutinin and neuraminidase cytoplasmic tails control particle shape. *EMBO J.* 16, 1236-1247. doi: 10.1093/emboj/16.6.1236

Kida et al., 1983, Inhibition of virus-induced hemolysis with monoclonal antibodies to different antigenic areas on the hemagglutinin molecule of A/seal/Massachusetts/1/80 (H7N7) influenza virus Kilbourne, 1976, Comparative efficacy of neuraminidase-specific and conventional influenza virus vaccines in induction of antibody to neuraminidase in humans, J Infect Dis., 134(4):384-94. doi: 10.1093/infdis/134.4.384

Kirkpatrick E. et al., 2018, The influenza virus hemagglutinin head evolves faster than the stalk domain, Scientific Reports, 8:10432, 1-14

Krystal M, et al., 1982, of structural features in the hemagglutinin genes, Proc Natl Acad Sci USA. 1982; 79:4800-4804

McAuley J. L. et al., 2019, Influenza Virus Neuraminidase Structure and Functions, Front Microbiol., 10, 39, Mintaev et al., 2014, Co-evolution analysis to predict protein-protein interactions within influenza virus envelope. *J. Bioinforma. Comput. Biol.* 12:1441008. doi: 10.1142/S021972001441008X Mitnaul et al., 1996; The cytoplasmic tail of influenza A virus neuraminidase (NA) affects NA incorporation into virions, virion morphology, and virulence in mice but is not essential for virus replication. *J. Virol.* 70, 873-879.

Morokutti A. et al., 2014, Intranasal vaccination with a replication-deficient influenza virus induces heterosubtypic neutralising mucosal IgA antibodies in humans, Vaccine, 32(17), 1897-1900

Moules et al., 2010, In vitro characterization of naturally occurring influenza H3NA-viruses lacking the NA gene segment: toward a new mechanism of viral resistance? *Virology* 404, 215-224. doi: 10.1016/j.virol.2010.04.030

Mueller et al, 2010, Immunization with live attenuated influenza viruses that express altered NS1 proteins results in potent and protective memory CD8+ T-cell responses, J Virol., 84:1847-55

Nemeroff M. et al., 1992, Identification of cis-acting intron and exon regions in influenza virus NS1 mRNA that inhibit splicing and cause the formation of aberrantly sedimenting presplicing complexes, Mol. Cell. Biol., 962-970

Nicolodi et al., 2019, Safety and immunogenicity of a replication-deficient H5N1 influenza virus vaccine lacking NS1, Vaccine, 37, 3722-372

Plotch S. and Krug R., 1986, In vitro splicing of influenza viral NS1 mRNA and NS1-beta-globin chimeras: possible mechanisms for the control of viral mRNA splicing Proc. Natl. Acad. Sci., 83, 5444-5448

Wiley et al., 1981, Structural identification of the antibody-binding sites of Hong Kong influenza haemagglutinin and their involvement in antigenic variation, Nature 289, 373-378

Varghese et al., 1983; Structure of the influenza virus glycoprotein antigen neuraminidase at 2.9 A resolution. Nature 303, 35-40, doi: 10.1038/303035a0

Wachek V. et al., J. Infect. Dis., 2010, 201(3), 354-62

Wang T T, et al., PLoS Pathog. 2010; 6:e1000796

Ward et al., 1983; The disulphide bonds of an Asian influenza virus neuraminidase. *FEBS Lett.* 153, 29-33. doi: 10.1016/0014-5793(83)80113-6

Yasugi M, et al., 2013, Human monoclonal antibodies broadly neutralizing against influenza B virus, PLoS Pathog. 9:e10031

The invention claimed is:

1. A recombinant influenza virus comprising a modified NS segment, encoding:

a) a fusion protein comprising from N to C-terminus:

- a truncated NS1 protein consisting of 10 to 20 amino acids of the N-terminus of the respective wild type NS1 protein,
- optionally a linker sequence,
- optionally a 2A self-cleaving peptide, specifically a P2A sequence,
- a signal peptide,
- a SARS-COV receptor binding domain (RBD) comprising up to 40, up to 30, or up to 27 amino acids of the C-terminal of the SARS-COV S1 subunit, and b) an NS2 protein.

2. The recombinant influenza virus of claim 1, wherein said virus is a human influenza B virus.

3. The recombinant influenza virus of claim 1, wherein the truncated NS1 protein comprises up to 16 of its N-terminal 10 to 18 amino acids.

4. The recombinant influenza virus of claim 1, comprising SEQ ID Nos: 1-6 or SEQ ID Nos: 54-57.

5. The recombinant influenza virus of claim 1, wherein the linker is a GS linker having a length of 2 to 10 amino acids.

6. The recombinant influenza virus of claim 1, comprising modifications of the NA and/or HA proteins.

7. The recombinant influenza virus of claim 1, wherein the RBD is fused to a transmembrane domain.

8. The recombinant influenza virus of claim 1, wherein the virus is combined with a physiologically acceptable excipient to form a pharmaceutical preparation.

9. The recombinant influenza virus claim 8, wherein the virus is present in the pharmaceutical preparation in an effective amount.

10. A method of providing prophylactic immunization against a disease condition which is caused by or associated with an infection by a coronavirus and/or influenza virus, comprising the step of administering an effective amount of the recombinant influenza virus of claim 1, wherein the immunity induced is effective in preventing infection of susceptible cells by the virus, thereby treating the disease condition.

11. The recombinant influenza virus of claim 8, wherein said pharmaceutical preparation is formulated for local administration to the upper and lower respiratory tract or for nasal, pulmonary, intraoral, ocular, or dermal administration, or for systemic parenteral administration.

12. The recombinant influenza virus of claim 8, wherein said pharmaceutical preparation is in the form of a spray, a powder, a gel, an ointment, a cream, a foam, or a liquid solution, a lotion, a patch, a gargle solution, an aerosolized powder, an aerosolized liquid formulation, granules, or capsules.

13. The recombinant influenza virus of claim 1, wherein the coronavirus is a B-coronavirus selected from the group consisting of SARS-COV-2, MERS-COV, SARS-COV-1, HCoV-OC43, and HCoV-HKU1, or mutants thereof.

14. An isolated nucleic acid sequence expressing the recombinant influenza virus of claim 1.

15. The nucleic acid sequence of claim 14, comprising one or more artificial splice sites within the gene encoding the truncated NS1 protein.

16. A method of vaccinating a subject with a two-component vaccine comprising the recombinant influenza virus of claim 1 with native hemagglutinin (HA) from Victoria or Yamagata lineages, comprising:

- administering a priming composition comprising one, two or three recombinant influenza virus strains of claim 1, and
- administering a boosting composition comprising one, two or three recombinant influenza virus strains of claim 1, wherein the influenza virus strains of the boosting composition comprise HA which antigenically differ from the HA of the influenza virus strains of the priming composition.

17. The method of claim 16, wherein the HA head of the influenza virus strains of the priming composition is antigenically different from the HA head of the influenza virus strains of the boosting composition.

18. The method of claim 16, wherein the boosting composition is administered 2 to 8 weeks after the priming composition.

19. The method of claim 16, wherein the boosting composition is administered about 3 weeks after the priming composition.

20. The method of claim 16, wherein the recombinant influenza virus of the priming composition comprises a native HA with a B/Victoria derived HA, and the recombinant influenza virus of the boosting composition comprises a native HA with a B/Yamagata lineage HA, or wherein the recombinant influenza virus of the priming composition comprises a native HA with a B/Victoria lineage derived HA, and the recombinant influenza virus of the boosting composition comprises a native HA with a B/Yamagata lineage derived HA.

* * * * *

SEQUENCE LISTING

```
<160> NUMBER OF SEQ ID NOS: 57

<210> SEQ ID NO 1
<211> LENGTH: 219
<212> TYPE: PRT
<213> ORGANISM: Artificial Sequence
<220> FEATURE:
<223> OTHER INFORMATION: Wuhan-Hu-1/2019 Reference strain (GenBank
      MN908947)

<400> SEQUENCE: 1

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190
```

```
Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215


<210> SEQ ID NO 2
<211> LENGTH: 219
<212> TYPE: PRT
<213> ORGANISM: Artificial Sequence
<220> FEATURE:
<223> OTHER INFORMATION: hCoV-19/Austria/CeMM0639/2020 (EPI_ISL_475936)

<400> SEQUENCE: 2

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215


<210> SEQ ID NO 3
<211> LENGTH: 219
<212> TYPE: PRT
<213> ORGANISM: Artificial Sequence
<220> FEATURE:
<223> OTHER INFORMATION: hCoV-19/Sweden/20-51988/2020 (EPI_ISL_4755690)

<400> SEQUENCE: 3

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
```

-continued

```
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215


<210> SEQ ID NO 4
<211> LENGTH: 219
<212> TYPE: PRT
<213> ORGANISM: Artificial Sequence
<220> FEATURE:
<223> OTHER INFORMATION: hCoV-19/Singapore/397/2020 (EPI_ISL_469146)

<400> SEQUENCE: 4

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
```

```
        195                 200                 205

Val Asn Phe Asn Phe Asn Gly Leu Thr Gly Thr
    210                 215


<210> SEQ ID NO 5
<211> LENGTH: 194
<212> TYPE: PRT
<213> ORGANISM: Artificial Sequence
<220> FEATURE:
<223> OTHER INFORMATION: hCoV-19/USA/IL-NM0118/2020 (EPI_ISL_444601)

<400> SEQUENCE: 5

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val


<210> SEQ ID NO 6
<211> LENGTH: 219
<212> TYPE: PRT
<213> ORGANISM: Artificial Sequence
<220> FEATURE:
<223> OTHER INFORMATION: SARS CoV-2 RBD amino acid sequence inserted
      (RBD219, see scheme in Fig.1)

<400> SEQUENCE: 6

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80
```

-continued

```
Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215
```

<210> SEQ ID NO 7
<211> LENGTH: 1325
<212> TYPE: DNA
<213> ORGANISM: Artificial Sequence
<220> FEATURE:
<223> OTHER INFORMATION: BGHB delNS-RBD219 BSMBI spm1

<400> SEQUENCE: 7

```
cgtctcaggg agcagaagca gaggatttgt ttagtcactg gcaaacagga aaaatggcgg     60

acaatatgac cacaacacaa attgaggtgg gtccgggagc aggatccgga gcaacaaatt    120

tctcacttct taaacaagca ggggacgtgg aagaaaatcc aggaccaatg aaaacagata    180

cacttcttct ttgggtgctg cttttgtggg ttccaagatc acatgggaat atcacgaatc    240

tgtgcccctt tggagaggtg ttcaatgcta cccgctttgc ttcagtgtac gcttggaata    300

ggaaacggat cagtaattgc gtggctgatt attctgtgct gtacaatagc gcaagcttca    360

gcacattcaa atgctatgga gtgagcccca caaaactgaa tgatctgtgc ttcactaatg    420

tttacgccga ttcatttgtg atacgcggag atgaggtgag acagattgcc cctggccaaa    480

caggaaaaat cgcggattac aattacaaac tgccagatga tttcactgga tgcgtgattg    540

catggaattc aaataatctg gatagtaaag ttggaggcaa ttacaattac ctgtacagac    600

tgttcagaaa aagcaatctg aaaccctttg agcgagatat cagcaccgaa atctaccagg    660

ctggctctac gccttgcaat ggagtggagg gattcaattg ttattttcct ctgcagagtt    720

acggattcca accgaccaat ggtgtgggat atcagcccta cagagtggtg gtgctgagct    780

tcgaactgct tcacgctcca gcaacagtgt gcggacccaa aaaatctact aatctggtga    840

aaaataagtg cgtgaatttc aatttcaatg gactgacggg aacgtaatga tgagcggccg    900

cccaagcaga aagtggtact aaccttcttc tctttcttct cctgacagtg gaggatgaag    960

aagatggcca tcggatcctc aattcactct tcgagcgtct taatgaagga cattcaaagc   1020

caattcgagc agctgaaact gcggtgggag tcttatccca atttggtcaa gagcaccgat   1080

tatcaccaga agagggagac aattagactg gtcacggaag aactttatct tttaagtaaa   1140

agaattgatg ataacatatt gttccacaaa acagtaatag ctaacagctc cataatagct   1200

gacatggttg tatcattatc attattagaa acattgtatg aaatgaagga tgtggttgaa   1260
```

-continued gtgtacagca ggcagtgctt gtgaatttaa aataaaaatc ctcttgttac tactaatacg 1320
agacg 1325

<210> SEQ ID NO 8
<211> LENGTH: 19
<212> TYPE: PRT
<213> ORGANISM: Artificial Sequence
<220> FEATURE:
<223> OTHER INFORMATION: P2A Sequence (all in frame)

<400> SEQUENCE: 8

Ala Thr Asn Phe Ser Leu Leu Lys Gln Ala Gly Asp Val Glu Glu Asn
1 5 10 15

Pro Gly Pro

<210> SEQ ID NO 9
<211> LENGTH: 8
<212> TYPE: PRT
<213> ORGANISM: Artificial Sequence
<220> FEATURE:
<223> OTHER INFORMATION: peptides
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 9

Asp Xaa Glu Xaa Asn Pro Gly Pro
1 5

<210> SEQ ID NO 10
<211> LENGTH: 11
<212> TYPE: DNA
<213> ORGANISM: Artificial Sequence
<220> FEATURE:
<223> OTHER INFORMATION: linker

<400> SEQUENCE: 10
caggtagatt g 11

<210> SEQ ID NO 11
<211> LENGTH: 11
<212> TYPE: DNA
<213> ORGANISM: Artificial Sequence
<220> FEATURE:
<223> OTHER INFORMATION: linker

<400> SEQUENCE: 11
caggtaagta t 11

<210> SEQ ID NO 12
<211> LENGTH: 11
<212> TYPE: DNA
<213> ORGANISM: Artificial Sequence
<220> FEATURE:
<223> OTHER INFORMATION: linker

<400> SEQUENCE: 12
caggtaaatt g 11

<210> SEQ ID NO 13
<211> LENGTH: 11

-continued

<212> TYPE: DNA
<213> ORGANISM: Artificial Sequence
<220> FEATURE:
<223> OTHER INFORMATION: linker

<400> SEQUENCE: 13
gaggtgggtc c 11

<210> SEQ ID NO 14
<211> LENGTH: 11
<212> TYPE: DNA
<213> ORGANISM: Artificial Sequence
<220> FEATURE:
<223> OTHER INFORMATION: linker

<400> SEQUENCE: 14
gaggtaggtc c 11

<210> SEQ ID NO 15
<211> LENGTH: 32
<212> TYPE: DNA
<213> ORGANISM: Artificial Sequence
<220> FEATURE:
<223> OTHER INFORMATION: linker

<400> SEQUENCE: 15
tactaacctt cttctctttc ttctcctgac ag 32

<210> SEQ ID NO 16
<211> LENGTH: 1097
<212> TYPE: DNA
<213> ORGANISM: Artificial Sequence
<220> FEATURE:
<223> OTHER INFORMATION: Influenza B/Thueringen/02/06 wild-type NS segment nucleotide sequence

<400> SEQUENCE: 16
agcagaagca gaggatttgt ttagtcactg gcaaacagga aaaatggcgg acaatatgac 60
cacaacacaa attgaggtgg gtccgggagc aaccaatgcc accataaact ttgaagcagg 120
aattctggag tgctatgaaa gactttcatg gcaaagggcc cttgactacc ctggtcaaga 180
ccgcctaaac agactaaaga gaaaattaga gtcaagaata aagactcaca acaaaagtga 240
gcctgaaagt aaaaggatgt ctcttgaaga gagaaaagca attggagtaa aaatgatgaa 300
agtactccta tttatgaatc cgtctgctgg aattgaaggg tttgagccat actgtatgaa 360
aagttcctca aagagcaact gtccgaaata caattggatc gattaccctt caaccccagg 420
gaggtgcctt gatgacatag aagaagaacc agatgatgtt gatggcccaa ctgaaatagt 480
attaagggac atgaacaaca aagatgcaag gcaaaagata aaggaggaag taaacactca 540
gaaagaaggg aagttccgtt tgacaataaa aagggatatg cgtaatgtat tgtccctgag 600
agtgttagta aacggaacat tcctcaaaca ccccaatggg tacaagtcct tatcaactct 660
gcatagattg aatgcatatg accagagtgg aaggcttgtt gctaaacttg ttgctactga 720
tgatcttaca gtggaggatg aagaagatgg ccatcggatc ctcaattcac tcttcgagcg 780
tcttaatgaa ggacattcaa agccaattcg agcagctgaa actgcggtgg gagtcttatc 840
ccaatttggt caagagcacc gattatcacc agaagaggga gacaattaga ctggtcacgg 900
aagaacttta tcttttaagt aaaagaattg atgataacat attgttccac aaaacagtaa 960
tagctaacag ctccataata gctgacatgg ttgtatcatt atcattatta gaaacattgt 1020
atgaaatgaa ggatgtggtt gaagtgtaca gcaggcagtg cttgtgaatt taaaataaaa 1080
atcctcttgt tactact 1097

<210> SEQ ID NO 17
<211> LENGTH: 5
<212> TYPE: PRT
<213> ORGANISM: Artificial Sequence
<220> FEATURE:
<223> OTHER INFORMATION: linker

<400> SEQUENCE: 17

Gly Gly Ser Gly Gly
1 5

<210> SEQ ID NO 18
<211> LENGTH: 5
<212> TYPE: PRT
<213> ORGANISM: Artificial Sequence
<220> FEATURE:
<223> OTHER INFORMATION: linker

<400> SEQUENCE: 18

Gly Ser Gly Ser Gly
1 5

<210> SEQ ID NO 19
<211> LENGTH: 8
<212> TYPE: PRT
<213> ORGANISM: Artificial Sequence
<220> FEATURE:
<223> OTHER INFORMATION: linker

<400> SEQUENCE: 19

Gly Ser Gly Ser Gly Ser Gly Ser
1 5

<210> SEQ ID NO 20
<211> LENGTH: 281
<212> TYPE: PRT
<213> ORGANISM: Artificial Sequence
<220> FEATURE:
<223> OTHER INFORMATION: Influenza B Thueringen/02/06 wild-type NS1
amino acid sequence

<400> SEQUENCE: 20

Met Ala Asp Asn Met Thr Thr Thr Gln Ile Glu Val Gly Pro Gly Ala
1 5 10 15

Thr Asn Ala Thr Ile Asn Phe Glu Ala Gly Ile Leu Glu Cys Tyr Glu
20 25 30

Arg Leu Ser Trp Gln Arg Ala Leu Asp Tyr Pro Gly Gln Asp Arg Leu
35 40 45

Asn Arg Leu Lys Arg Lys Leu Glu Ser Arg Ile Lys Thr His Asn Lys
50 55 60

Ser Glu Pro Glu Ser Lys Arg Met Ser Leu Glu Glu Arg Lys Ala Ile
65 70 75 80

Gly Val Lys Met Met Lys Val Leu Leu Phe Met Asn Pro Ser Ala Gly
85 90 95

Ile Glu Gly Phe Glu Pro Tyr Cys Met Lys Ser Ser Ser Lys Ser Asn
100 105 110

Cys Pro Lys Tyr Asn Trp Ile Asp Tyr Pro Ser Thr Pro Gly Arg Cys
115 120 125

Leu Asp Asp Ile Glu Glu Glu Pro Asp Asp Val Asp Gly Pro Thr Glu
130 135 140

```
Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Lys
                165                 170                 175

Arg Asp Met Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
    210                 215                 220

Thr Asp Asp Leu Thr Val Glu Asp Glu Glu Asp Gly His Arg Ile Leu
225                 230                 235                 240

Asn Ser Leu Phe Glu Arg Leu Asn Glu Gly His Ser Lys Pro Ile Arg
                245                 250                 255

Ala Ala Glu Thr Ala Val Gly Val Leu Ser Gln Phe Gly Gln Glu His
            260                 265                 270

Arg Leu Ser Pro Glu Glu Gly Asp Asn
        275                 280


<210> SEQ ID NO 21
<211> LENGTH: 4
<212> TYPE: PRT
<213> ORGANISM: Artificial Sequence
<220> FEATURE:
<223> OTHER INFORMATION: linker

<400> SEQUENCE: 21

Gly Gly Gly Gly
1


<210> SEQ ID NO 22
<211> LENGTH: 752
<212> TYPE: PRT
<213> ORGANISM: Artificial Sequence
<220> FEATURE:
<223> OTHER INFORMATION: B/Thueringen/02/06 amino acid sequence PB1 D67N

<400> SEQUENCE: 22

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Val Ser Asp Ile Thr Gly Cys Thr
    50                  55                  60

Met Ile Asn Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
```

-continued

```
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Ser Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
        275                 280                 285

Met Leu Ser Asn Cys Pro Pro Gly Gly Ile Ser Met Thr Val Thr Gly
    290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Arg Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Ile Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575
```

-continued

```
Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Arg Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735

Asp Asp Phe Glu Lys Ala Met Ala His Leu Gly Glu Ile Gly Tyr Thr
            740                 745                 750


<210> SEQ ID NO 23
<211> LENGTH: 248
<212> TYPE: PRT
<213> ORGANISM: Artificial Sequence
<220> FEATURE:
<223> OTHER INFORMATION: B/Thueringen/02/06, amino acid sequence M1 K93R

<400> SEQUENCE: 23

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Arg Lys Gly Leu
                85                  90                  95

Ile Leu Ala Glu Arg Lys Met Arg Lys Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190
```

```
Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245


<210> SEQ ID NO 24
<211> LENGTH: 119
<212> TYPE: PRT
<213> ORGANISM: Artificial Sequence
<220> FEATURE:
<223> OTHER INFORMATION: B/Thueringen/02/06 BGHB ?NS, amino acid
      sequence NS2 Y117H

<400> SEQUENCE: 24

Met Ala Asp Asn Met Thr Thr Thr Gln Ile Glu Trp Arg Met Lys Lys
1               5                   10                  15

Met Ala Ile Gly Ser Ser Ile His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Arg Ile Asp Asp Asn
65                  70                  75                  80

Ile Leu Phe His Lys Thr Val Ile Ala Asn Ser Ser Ile Ile Ala Asp
                85                  90                  95

Met Val Val Ser Leu Ser Leu Leu Glu Thr Leu Tyr Glu Met Lys Asp
            100                 105                 110

Val Val Glu Val His Ser Arg
        115


<210> SEQ ID NO 25
<211> LENGTH: 277
<212> TYPE: PRT
<213> ORGANISM: Artificial Sequence
<220> FEATURE:
<223> OTHER INFORMATION: protein

<400> SEQUENCE: 25

Met Ala Asp Asn Met Thr Thr Thr Gln Ile Glu Val Gly Pro Gly Ala
1               5                   10                  15

Gly Ser Gly Ala Thr Asn Phe Ser Leu Leu Lys Gln Ala Gly Asp Val
            20                  25                  30

Glu Glu Asn Pro Gly Pro Met Lys Thr Asp Thr Leu Leu Leu Trp Val
        35                  40                  45

Leu Leu Leu Trp Val Pro Arg Ser His Gly Asn Ile Thr Asn Leu Cys
    50                  55                  60

Pro Phe Gly Glu Val Phe Asn Ala Thr Arg Phe Ala Ser Val Tyr Ala
65                  70                  75                  80

Trp Asn Arg Lys Arg Ile Ser Asn Cys Val Ala Asp Tyr Ser Val Leu
                85                  90                  95

Tyr Asn Ser Ala Ser Phe Ser Thr Phe Lys Cys Tyr Gly Val Ser Pro
            100                 105                 110
```

-continued

Thr Lys Leu Asn Asp Leu Cys Phe Thr Asn Val Tyr Ala Asp Ser Phe
        115                 120                 125

Val Ile Arg Gly Asp Glu Val Arg Gln Ile Ala Pro Gly Gln Thr Gly
    130                 135                 140

Lys Ile Ala Asp Tyr Asn Tyr Lys Leu Pro Asp Asp Phe Thr Gly Cys
145                 150                 155                 160

Val Ile Ala Trp Asn Ser Asn Asn Leu Asp Ser Lys Val Gly Gly Asn
                165                 170                 175

Tyr Asn Tyr Leu Tyr Arg Leu Phe Arg Lys Ser Asn Leu Lys Pro Phe
            180                 185                 190

Glu Arg Asp Ile Ser Thr Glu Ile Tyr Gln Ala Gly Ser Thr Pro Cys
        195                 200                 205

Asn Gly Val Glu Gly Phe Asn Cys Tyr Phe Pro Leu Gln Ser Tyr Gly
    210                 215                 220

Phe Gln Pro Thr Asn Gly Val Gly Tyr Gln Pro Tyr Arg Val Val Val
225                 230                 235                 240

Leu Ser Phe Glu Leu Leu His Ala Pro Ala Thr Val Cys Gly Pro Lys
                245                 250                 255

Lys Ser Thr Asn Leu Val Lys Asn Lys Cys Val Asn Phe Asn Phe Asn
            260                 265                 270

Gly Leu Thr Gly Thr
        275

<210> SEQ ID NO 26
<211> LENGTH: 16
<212> TYPE: PRT
<213> ORGANISM: Artificial Sequence
<220> FEATURE:
<223> OTHER INFORMATION: C-terminally truncated NS1

<400> SEQUENCE: 26

Met Ala Asp Asn Met Thr Thr Thr Gln Ile Glu Val Gly Pro Gly Ala
1               5                   10                  15

<210> SEQ ID NO 27
<211> LENGTH: 20
<212> TYPE: PRT
<213> ORGANISM: Artificial Sequence
<220> FEATURE:
<223> OTHER INFORMATION: signal peptide

<400> SEQUENCE: 27

Met Lys Thr Asp Thr Leu Leu Leu Trp Val Leu Leu Leu Trp Val Pro
1               5                   10                  15

Arg Ser His Gly
            20

<210> SEQ ID NO 28
<211> LENGTH: 219
<212> TYPE: PRT
<213> ORGANISM: Artificial Sequence
<220> FEATURE:
<223> OTHER INFORMATION: SARS-CoV-2 RBD sequence

<400> SEQUENCE: 28

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys

```
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215


<210> SEQ ID NO 29
<211> LENGTH: 657
<212> TYPE: DNA
<213> ORGANISM: Artificial Sequence
<220> FEATURE:
<223> OTHER INFORMATION: RBD219 (nt 22553-23209 in SARS-CoV-2 reference
      strain hCoV-19/Wuhan/Hu-1/2019 EPI ISL 402125, S Protein is nt
      21536-25384)

<400> SEQUENCE: 29

aatattacaa acttgtgccc ttttggtgaa gtttttaacg ccaccagatt tgcatctgtt      60

tatgcttgga acaggaagag aatcagcaac tgtgttgctg attattctgt cctatataat     120

tccgcatcat ttccactttt taagtgttat ggagtgtctc ctactaaatt aaatgatctc     180

tgctttacta atgtctatgc agattcattt gtaattagag gtgatgaagt cagacaaatc     240

gctccagggc aaactggaaa gattgctgat tataattata aattaccaga tgattttaca     300

ggctgcgtta tagcttggaa ttctaacaat cttgattcta aggttggtgg taattataat     360

tacctgtata gattgtttag gaagtctaat ctcaaacctt ttgagagaga tatttcaact     420

gaaatctatc aggccggtag cacaccttgt aatggtgttg aaggttttaa ttgttacttt     480

cctttacaat catatggttt ccaacccact aatggtgttg gttaccaacc atacagagta     540

gtagtacttt cttttgaact tctacatgca ccagcaactg tttgtggacc taaaaagtct     600

actaatttgg ttaaaaacaa atgtgtcaat ttcaacttca atggtttaac aggcaca        657


<210> SEQ ID NO 30
<211> LENGTH: 219
<212> TYPE: PRT
<213> ORGANISM: Artificial Sequence
<220> FEATURE:
<223> OTHER INFORMATION: Amino Acid Sequence is AA 331-524 in the S
      Protein of the reference strain

<400> SEQUENCE: 30
```

-continued

```
Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215

<210> SEQ ID NO 31
<211> LENGTH: 669
<212> TYPE: DNA
<213> ORGANISM: Artificial Sequence
<220> FEATURE:
<223> OTHER INFORMATION: RBD223 (nt 22517- 23185 in SARS-CoV-2 reference
      strain hCoV-19/Wuhan/Hu-1/2019 EPI ISL 402125, S Protein is nt
      21536-25384)

<400> SEQUENCE: 31

agagtccagc cgaccgaatc tattgttaga tttcctaata tcacgaatct gtgccccttt      60

ggagaggtgt tcaatgctac ccgctttgct tcagtgtacg cttggaatag gaaacggatc     120

agtaattgcg tggctgatta ttctgtgctg tacaatagcg caagcttcag cacattcaaa     180

tgctatggag tgagccccac aaaactgaat gatctgtgct tcactaatgt ttacgccgat     240

tcatttgtga tacgcggaga tgaggtgaga cagattgccc ctggccaaac aggaaaaatc     300

gcggattaca attacaaact gccagatgat ttcactggat gcgtgattgc atggaattca     360

aataatctgg atagtaaagt tggaggcaat tacaattacc tgtacagact gttcagaaaa     420

agcaatctga aaccctttga gcgagatatc agcaccgaaa tctaccaggc tggctctacg     480

ccttgcaatg gagtggaggg attcaattgt tattttcctc tgcagagtta cggattccaa     540

ccgaccaatg gtgtgggata tcagccctac agagtggtgg tgctgagctt cgaactgctt     600

cacgctccag caacagtgtg cggacccaaa aatctacta atctggtgaa aaataagtgc     660

gtgaatttc                                                              669
```

```
<210> SEQ ID NO 32
<211> LENGTH: 223
<212> TYPE: PRT
<213> ORGANISM: Artificial Sequence
<220> FEATURE:
<223> OTHER INFORMATION: Amino Acid Sequence is AA 319-514 in the S
      protein of the reference strain

<400> SEQUENCE: 32

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 33
<211> LENGTH: 26
<212> TYPE: PRT
<213> ORGANISM: Artificial Sequence
<220> FEATURE:
<223> OTHER INFORMATION: Amino Acid: Transmembrane Domain

<400> SEQUENCE: 33

Leu Leu Tyr Tyr Ser Thr Ala Ala Ser Ser Leu Ala Val Thr Leu Met
1               5                   10                  15

Leu Ala Ile Phe Ile Val Tyr Met Val Ser
            20                  25


<210> SEQ ID NO 34
<211> LENGTH: 10
<212> TYPE: PRT
<213> ORGANISM: Artificial Sequence
<220> FEATURE:
<223> OTHER INFORMATION: Amino Acid: Cytoplasmic Tail

<400> SEQUENCE: 34
```

-continued

```
Arg Asp Asn Val Ser Cys Ser Ile Cys Leu
1               5                   10


<210> SEQ ID NO 35
<211> LENGTH: 78
<212> TYPE: DNA
<213> ORGANISM: Artificial Sequence
<220> FEATURE:
<223> OTHER INFORMATION: Nucleotide: Transmembrane Domain

<400> SEQUENCE: 35

ctgctctatt actcaactgc tgcttctagt ttggctgtaa cattaatgct agctattttt     60

attgtttata tggtctcc                                                   78


<210> SEQ ID NO 36
<211> LENGTH: 30
<212> TYPE: DNA
<213> ORGANISM: Artificial Sequence
<220> FEATURE:
<223> OTHER INFORMATION: Nucleotide: Cytoplasmic Tail

<400> SEQUENCE: 36

agagacaacg tttcatgctc catctgtcta                                      30


<210> SEQ ID NO 37
<211> LENGTH: 27
<212> TYPE: PRT
<213> ORGANISM: Artificial Sequence
<220> FEATURE:
<223> OTHER INFORMATION: Flu A (A/Texas/04/2009) HA2 Transmembrane
      domain and Cytoplasmic Tail Amino Acid:Transmembrane Domain

<400> SEQUENCE: 37

Gln Ile Leu Ala Ile Tyr Ser Thr Val Ala Ser Ser Leu Val Leu Val
1               5                   10                  15

Val Ser Leu Gly Ala Ile Ser Phe Trp Met Cys
            20                  25


<210> SEQ ID NO 38
<211> LENGTH: 11
<212> TYPE: PRT
<213> ORGANISM: Artificial Sequence
<220> FEATURE:
<223> OTHER INFORMATION: Flu A (A/Texas/04/2009) HA2 Transmembrane
      domain and Cytoplasmic Tail Amino Acid:Cytoplasmic Tail

<400> SEQUENCE: 38

Ser Asn Gly Ser Leu Gln Cys Arg Ile Cys Ile
1               5                   10


<210> SEQ ID NO 39
<211> LENGTH: 80
<212> TYPE: DNA
<213> ORGANISM: Artificial Sequence
<220> FEATURE:
<223> OTHER INFORMATION: Flu A (A/Texas/04/2009) HA2 Transmembrane
      domain and Cytoplasmic Tail Nucleotide:Transmembrane Domain

<400> SEQUENCE: 39

agattttggc gatctattca actgtcgcca gttcattggt actggtagtc tccctggggg     60

caatcagttt ctggatgtgc                                                 80


<210> SEQ ID NO 40
<211> LENGTH: 33
<212> TYPE: DNA
```

-continued

<213> ORGANISM: Artificial Sequence
<220> FEATURE:
<223> OTHER INFORMATION: Flu A (A/Texas/04/2009) HA2 Transmembrane
domain and Cytoplasmic Tail Nucleotide:Cytoplasmic Tail

<400> SEQUENCE: 40
tctaatgggt ctctacagtg tagaatatgt att 33

<210> SEQ ID NO 41
<211> LENGTH: 1442
<212> TYPE: DNA
<213> ORGANISM: Artificial Sequence
<220> FEATURE:
<223> OTHER INFORMATION: BGHB delNS1-RBD219 BSMBI plus Flu B HA2 linker,
transmembrane domain, and cytoplasmic tail from B/Phuket/3073/2013
(Codon optimized) nucleotide sequence

<400> SEQUENCE: 41
agggagcaga agcagaggat ttgtttagtc actggcaaac aggaaaaatg gcggacaata 60
tgaccacaac acaaattgag gtgggtccgg gagcaggatc cggagcaaca aatttctcac 120
ttcttaaaca agcaggggac gtggaagaaa atccaggacc aatgaaaaca gatacacttc 180
ttctttgggt gctgcttttg tgggttccaa gatcacatgg gaatatcacg aatctgtgcc 240
cctttggaga ggtgttcaat gctacccgct ttgcttcagt gtacgcttgg aataggaaac 300
ggatcagtaa ttgcgtggct gattattctg tgctgtacaa tagcgcaagc ttcagcacat 360
tcaaatgcta tggagtgagc cccacaaaac tgaatgatct gtgcttcact aatgtttacg 420
ccgattcatt tgtgatacgc ggagatgagg tgagacagat tgcccctggc caaacaggaa 480
aaatcgcgga ttacaattac aaactgccag atgatttcac tggatgcgtg attgcatgga 540
attcaaataa tctggatagt aaagttggag gcaattacaa ttacctgtac agactgttca 600
gaaaaagcaa tctgaaaccc tttgagcgag atatcagcac cgaaatctac caggctggct 660
ctacgccttg caatggagtg gagggattca attgttattt tcctctgcag agttacggat 720
tccaaccgac caatggtgtg ggatatcagc cctacagagt ggtggtgctg agcttcgaac 780
tgcttcacgc tccagcaaca gtgtgcggac ccaaaaaatc tactaatctg gtgaaaaata 840
agtgcgtgaa tttcaatttc aatggactga cgggaacggg attggataat catactatac 900
tgctttacta ctcaactgct gcctccagtt tggctgtaac actgatgata gctatctttg 960
ttgtttatat ggtctccaga gacaatgttt cttgctccat ctgtctataa tgatgagcgg 1020
ccgcccaagc agaaagtggt actaaccttc ttctctttct tctcctgaca gtggaggatg 1080
aagaagatgg ccatcggatc ctcaattcac tcttcgagcg tcttaatgaa ggacattcaa 1140
agccaattcg agcagctgaa actgcggtgg gagtcttatc ccaatttggt caagagcacc 1200
gattatcacc agaagaggga gacaattaga ctggtcacgg aagaacttta tcttttaagt 1260
aaaagaattg atgataacat attgttccac aaaacagtaa tagctaacag ctccataata 1320
gctgacatgg ttgtatcatt atcattatta gaaacattgt atgaaatgaa ggatgtggtt 1380
gaagtgtaca gcaggcagtg cttgtgaatt taaaataaaa atcctcttgt tactactaat 1440
ac 1442

<210> SEQ ID NO 42
<211> LENGTH: 122
<212> TYPE: PRT
<213> ORGANISM: Artificial Sequence
<220> FEATURE:
<223> OTHER INFORMATION: BGHB delNS1-RBD219 BSMBI plus Flu B HA2 linker,
transmembrane domain, and cytoplasmic tail from B/Phuket/3073/2013

(Codon optimized) amino acid sequence NEP/NS2 (spliced)

<400> SEQUENCE: 42

```
Met Ala Asp Asn Met Thr Thr Thr Gln Ile Glu Trp Arg Met Lys Lys
1               5                   10                  15

Met Ala Ile Gly Ser Ser Ile His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Arg Ile Asp Asp Asn
65                  70                  75                  80

Ile Leu Phe His Lys Thr Val Ile Ala Asn Ser Ser Ile Ile Ala Asp
                85                  90                  95

Met Val Val Ser Leu Ser Leu Leu Glu Thr Leu Tyr Glu Met Lys Asp
            100                 105                 110

Val Val Glu Val Tyr Ser Arg Gln Cys Leu
        115                 120
```

<210> SEQ ID NO 43
<211> LENGTH: 219
<212> TYPE: PRT
<213> ORGANISM: Artificial Sequence
<220> FEATURE:
<223> OTHER INFORMATION: SARS-CoV-2 RBD219

<400> SEQUENCE: 43

```
Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr
    210                 215
```

<210> SEQ ID NO 44
<211> LENGTH: 7
<212> TYPE: PRT
<213> ORGANISM: Artificial Sequence
<220> FEATURE:
<223> OTHER INFORMATION: Flu B HA2 Linker

<400> SEQUENCE: 44

Gly Leu Asp Asn His Thr Ile
1               5

<210> SEQ ID NO 45
<211> LENGTH: 1448
<212> TYPE: DNA
<213> ORGANISM: Artificial Sequence
<220> FEATURE:
<223> OTHER INFORMATION: BGHB delNS1-RBD219 BSMBI plus generic linker, Flu B HA2 transmembrane domain, and cytoplasmic tail from B/Phuket/3073/2013 (Codon optimized) nucleotide sequence

<400> SEQUENCE: 45
agggagcaga agcagaggat ttgtttagtc actggcaaac aggaaaaatg gcggacaata 60
tgaccacaac acaaattgag gtgggtccgg gagcaggatc cggagcaaca aatttctcac 120
ttcttaaaca agcaggggac gtggaagaaa atccaggacc aatgaaaaca gatacacttc 180
ttctttgggt gctgcttttg tgggttccaa gatcacatgg gaatatcacg aatctgtgcc 240
cctttggaga ggtgttcaat gctacccgct ttgcttcagt gtacgcttgg aataggaaac 300
ggatcagtaa ttgcgtggct gattattctg tgctgtacaa tagcgcaagc ttcagcacat 360
tcaaatgcta tggagtgagc cccacaaaac tgaatgatct gtgcttcact aatgtttacg 420
ccgattcatt tgtgatacgc ggagatgagg tgagacagat tgcccctggc caaacaggaa 480
aaatcgcgga ttacaattac aaactgccag atgatttcac tggatgcgtg attgcatgga 540
attcaaataa tctggatagt aaagttggag gcaattacaa ttacctgtac agactgttca 600
gaaaaagcaa tctgaaaccc tttgagcgag atatcagcac cgaaatctac caggctggct 660
ctacgccttg caatggagtg gagggattca attgttattt tcctctgcag agttacggat 720
tccaaccgac caatggtgtg ggatatcagc cctacagagt ggtggtgctg agcttcgaac 780
tgcttcacgc tccagcaaca gtgtgcggac ccaaaaaatc tactaatctg gtgaaaaata 840
agtgcgtgaa tttcaatttc aatggactga cgggaacggg tagtggtagt ggtagtggta 900
gtggtctgct ttactactca actgctgcct ccagtttggc tgtaacactg atgatagcta 960
tctttgttgt ttatatggtc tccagagaca atgtttcttg ctccatctgt ctataatgat 1020
gagcggccgc ccaagcagaa agtggtacta accttcttct ctttcttctc ctgacagtgg 1080
aggatgaaga agatggccat cggatcctca attcactctt cgagcgtctt aatgaaggac 1140
attcaaagcc aattcgagca gctgaaactg cggtgggagt cttatcccaa tttggtcaag 1200
agcaccgatt atcaccagaa gagggagaca attagactgg tcacggaaga actttatctt 1260
ttaagtaaaa gaattgatga taacatattg ttccacaaaa cagtaatagc taacagctcc 1320
ataatagctg acatggttgt atcattatca ttattagaaa cattgtatga aatgaaggat 1380
gtggttgaag tgtacagcag gcagtgcttg tgaatttaaa ataaaaatcc tcttgttact 1440
actaatac 1448

<210> SEQ ID NO 46
<211> LENGTH: 122

<212> TYPE: PRT
<213> ORGANISM: Artificial Sequence
<220> FEATURE:
<223> OTHER INFORMATION: BGHB delNS1-RBD219 BSMBI plus generic linker, Flu B HA2 transmembrane domain, and cytoplasmic tail from B/Phuket/3073/2013 (Codon optimized) amino acid sequence NEP/NS2 (spliced)

<400> SEQUENCE: 46

```
Met Ala Asp Asn Met Thr Thr Thr Gln Ile Glu Trp Arg Met Lys Lys
1               5                   10                  15

Met Ala Ile Gly Ser Ser Ile His Ser Ser Ser Val Leu Met Lys Asp
            20                  25                  30

Ile Gln Ser Gln Phe Glu Gln Leu Lys Leu Arg Trp Glu Ser Tyr Pro
        35                  40                  45

Asn Leu Val Lys Ser Thr Asp Tyr His Gln Lys Arg Glu Thr Ile Arg
    50                  55                  60

Leu Val Thr Glu Glu Leu Tyr Leu Leu Ser Lys Arg Ile Asp Asp Asn
65                  70                  75                  80

Ile Leu Phe His Lys Thr Val Ile Ala Asn Ser Ser Ile Ile Ala Asp
                85                  90                  95

Met Val Val Ser Leu Ser Leu Leu Glu Thr Leu Tyr Glu Met Lys Asp
            100                 105                 110

Val Val Glu Val Tyr Ser Arg Gln Cys Leu
        115                 120
```

<210> SEQ ID NO 47
<211> LENGTH: 219
<212> TYPE: PRT
<213> ORGANISM: Artificial Sequence
<220> FEATURE:
<223> OTHER INFORMATION: SARS-CoV-2 RBD219

<400> SEQUENCE: 47

```
Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190
```

Thr Val Cys Gly Pro Lys Lys Ser Thr Asn Leu Val Lys Asn Lys Cys
195 200 205

Val Asn Phe Asn Phe Asn Gly Leu Thr Gly Thr
210 215

<210> SEQ ID NO 48
<211> LENGTH: 9
<212> TYPE: PRT
<213> ORGANISM: Artificial Sequence
<220> FEATURE:
<223> OTHER INFORMATION: Generic Linker

<400> SEQUENCE: 48

Gly Ser Gly Ser Gly Ser Gly Ser Gly
1 5

<210> SEQ ID NO 49
<211> LENGTH: 6
<212> TYPE: PRT
<213> ORGANISM: Artificial Sequence
<220> FEATURE:
<223> OTHER INFORMATION: N-terminal domain sequence is nearly 100% conserved across all IAV subtypes

<400> SEQUENCE: 49

Met Asn Pro Asn Gln Lys
1 5

<210> SEQ ID NO 50
<211> LENGTH: 122
<212> TYPE: PRT
<213> ORGANISM: Artificial Sequence
<220> FEATURE:
<223> OTHER INFORMATION: Influenza B Thueringen/02/06 wild-type NEP/NS2 amino acid sequence

<400> SEQUENCE: 50

Met Ala Asp Asn Met Thr Thr Thr Gln Ile Glu Trp Arg Met Lys Lys
1 5 10 15

Met Ala Ile Gly Ser Ser Ile His Ser Ser Ser Val Leu Met Lys Asp
20 25 30

Ile Gln Ser Gln Phe Glu Gln Leu Lys Leu Arg Trp Glu Ser Tyr Pro
35 40 45

Asn Leu Val Lys Ser Thr Asp Tyr His Gln Lys Arg Glu Thr Ile Arg
50 55 60

Leu Val Thr Glu Glu Leu Tyr Leu Leu Ser Lys Arg Ile Asp Asp Asn
65 70 75 80

Ile Leu Phe His Lys Thr Val Ile Ala Asn Ser Ser Ile Ile Ala Asp
85 90 95

Met Val Val Ser Leu Ser Leu Leu Glu Thr Leu Tyr Glu Met Lys Asp
100 105 110

Val Val Glu Val Tyr Ser Arg Gln Cys Leu
115 120

<210> SEQ ID NO 51
<211> LENGTH: 890
<212> TYPE: DNA
<213> ORGANISM: Artificial Sequence
<220> FEATURE:
<223> OTHER INFORMATION: Influenza A/Puerto Rico/8/34 wild-type NS segment nucleotide sequence

<400> SEQUENCE: 51

```
agcaaaagca gggtgacaaa gacataatgg atccaaacac tgtgtcaagc tttcaggtag     60
attgctttct ttggcatgtc cgcaaacgag ttgcagacca agaactaggt gatgccccat    120
tccttgatcg gcttcgccga gatcagaaat ccctaagagg aaggggcagc accctcggtc    180
tggacatcga gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
aggatgtcaa aaatgcagtt ggagtcctca tcgggggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttaataataa aaaacaccct tgtttctact               890
```

<210> SEQ ID NO 52
<211> LENGTH: 230
<212> TYPE: PRT
<213> ORGANISM: Artificial Sequence
<220> FEATURE:
<223> OTHER INFORMATION: Influenza A/Puerto Rico/8/34 wild-type NS1 amino acid sequence

<400> SEQUENCE: 52

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
```

```
        195                 200                 205

Asn Gly Arg Pro Pro Leu Thr Pro Lys Gln Lys Arg Glu Met Ala Gly
    210                 215                 220

Thr Ile Arg Ser Glu Val
225                 230


<210> SEQ ID NO 53
<211> LENGTH: 121
<212> TYPE: PRT
<213> ORGANISM: Artificial Sequence
<220> FEATURE:
<223> OTHER INFORMATION: Influenza A/Puerto Rico/8/34 wild-type NEP/NS2
      amino acid sequence

<400> SEQUENCE: 53

Met Asp Pro Asn Thr Val Ser Ser Phe Gln Asp Ile Leu Leu Arg Met
1               5                   10                  15

Ser Lys Met Gln Leu Glu Ser Ser Ser Gly Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Ile Thr Glu Asn Ser Phe Glu Gln
                85                  90                  95

Ile Thr Phe Met Gln Ala Leu His Leu Leu Leu Glu Val Glu Gln Glu
            100                 105                 110

Ile Arg Thr Phe Ser Phe Gln Leu Ile
        115                 120


<210> SEQ ID NO 54
<211> LENGTH: 194
<212> TYPE: PRT
<213> ORGANISM: Artificial Sequence
<220> FEATURE:
<223> OTHER INFORMATION: SARS-CoV-2 RBD-219 Original Sequence

<400> SEQUENCE: 54

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140
```

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Asn Gly Val Gly Tyr Gln
165 170 175

Pro Tyr Arg Val Val Val Leu Ser Phe Glu Leu Leu His Ala Pro Ala
180 185 190

Thr Val

<210> SEQ ID NO 55
<211> LENGTH: 194
<212> TYPE: PRT
<213> ORGANISM: Artificial Sequence
<220> FEATURE:
<223> OTHER INFORMATION: SARS-CoV-2 RBD-219 Original Sequence: England Variant: N501Y

<400> SEQUENCE: 55

Asn Ile Thr Asn Leu Cys Pro Phe Gly Glu Val Phe Asn Ala Thr Arg
1 5 10 15

Phe Ala Ser Val Tyr Ala Trp Asn Arg Lys Arg Ile Ser Asn Cys Val
20 25 30

Ala Asp Tyr Ser Val Leu Tyr Asn Ser Ala Ser Phe Ser Thr Phe Lys
35 40 45

Cys Tyr Gly Val Ser Pro Thr Lys Leu Asn Asp Leu Cys Phe Thr Asn
50 55 60

Val Tyr Ala Asp Ser Phe Val Ile Arg Gly Asp Glu Val Arg Gln Ile
65 70 75 80

Ala Pro Gly Gln Thr Gly Lys Ile Ala Asp Tyr Asn Tyr Lys Leu Pro
85 90 95

Asp Asp Phe Thr Gly Cys Val Ile Ala Trp Asn Ser Asn Asn Leu Asp
100 105 110

Ser Lys Val Gly Gly Asn Tyr Asn Tyr Leu Tyr Arg Leu Phe Arg Lys
115 120 125

Ser Asn Leu Lys Pro Phe Glu Arg Asp Ile Ser Thr Glu Ile Tyr Gln
130 135 140

Ala Gly Ser Thr Pro Cys Asn Gly Val Glu Gly Phe Asn Cys Tyr Phe
145 150 155 160

Pro Leu Gln Ser Tyr Gly Phe Gln Pro Thr Tyr Gly Val Gly Tyr Gln
165 170 175

Pro Tyr Arg Val Val Val Leu Ser Phe Glu Leu Leu His Ala Pro Ala
180 185 190

Thr Val

<210> SEQ ID NO 56
<211> LENGTH: 194
<212> TYPE: PRT
<213> ORGANISM: Artificial Sequence
<220> FEATURE:
<223> OTHER INFORMATION: SARS-CoV-2 RBD-219 Original Sequence: South Africa Variant: K417N, E484K and N501Y

<400> SEQUENCE: 56

Asn Ile Thr Asn Leu Cys Pro Phe Gly Glu Val Phe Asn Ala Thr Arg
1 5 10 15

Phe Ala Ser Val Tyr Ala Trp Asn Arg Lys Arg Ile Ser Asn Cys Val
20 25 30

Ala Asp Tyr Ser Val Leu Tyr Asn Ser Ala Ser Phe Ser Thr Phe Lys

```
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Asn Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Lys Gly Phe Asn Cys Tyr Phe
145                 150                 155                 160

Pro Leu Gln Ser Tyr Gly Phe Gln Pro Thr Tyr Gly Val Gly Tyr Gln
                165                 170                 175

Pro Tyr Arg Val Val Val Leu Ser Phe Glu Leu Leu His Ala Pro Ala
            180                 185                 190

Thr Val


<210> SEQ ID NO 57
<211> LENGTH: 194
<212> TYPE: PRT
<213> ORGANISM: Artificial Sequence
<220> FEATURE:
<223> OTHER INFORMATION: SARS-CoV-2 RBD-219 Delta Variant: L452R and
      T478K

<400> SEQUENCE: 57

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Arg Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Lys Pro Cys Asn Gly Val Glu Gly Phe Asn Cys Tyr Phe
145                 150                 155                 160
```

-continued

```
Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val
```